United States Patent
Belfer et al.

(10) Patent No.: US 6,196,223 B1
(45) Date of Patent: Mar. 6, 2001

(54) STRAPLESS RESPIRATORY FACIAL MASK FOR CUSTOMIZING TO THE WEARER'S FACE

(76) Inventors: William A. Belfer, 804 West Park Ave.; Phillip Petillo, Herbert Ave., both of Ocean, NJ (US) 07712

( * ) Notice: Subject to any disclaimer, the term of this patent is extended or adjusted under 35 U.S.C. 154(b) by 0 days.

(21) Appl. No.: 09/301,876

(22) Filed: Apr. 29, 1999

Related U.S. Application Data

(63) Continuation-in-part of application No. 09/058,437, filed on Apr. 10, 1998.

(51) Int. Cl.$^7$ .................................................. A63B 18/08
(52) U.S. Cl. .................. 128/206.25; 128/205.25
(58) Field of Search .................. 128/206.14, 206.21, 128/206.24, 206.25, 206.28, 205.25, 200.24, 205.19

(56) References Cited

U.S. PATENT DOCUMENTS

| | | | |
|---|---|---|---|
| 2,809,633 | * | 10/1957 | Swearingen et al. ................ 128/146 |
| 4,069,516 | * | 1/1978 | Watkins, Jr. .............................. 2/428 |
| 4,467,799 | * | 8/1984 | Steinberg ......................... 128/206.14 |
| 5,003,633 | * | 4/1991 | Itoh ............................................... 2/9 |
| 5,143,061 | * | 9/1992 | Kaimer ............................ 128/206.24 |
| 5,884,624 | * | 3/1999 | Barnett et al. ................... 128/206.24 |
| 6,082,360 | * | 7/2000 | Rudolph et al. ................. 128/206.25 |

* cited by examiner

*Primary Examiner*—Aaron J. Lewis
*Assistant Examiner*—Teena Mitchell
(74) *Attorney, Agent, or Firm*—Ezra Sutton

(57) ABSTRACT

A strapless respiratory facial mask for attachment to the wearer's face including a moldable laminated gasket member having a cushioning layer and an adhesive layer for engaging the facial contours and skin of the wearer's face; and the gasket member having a central opening for receiving the nose of the wearer. The facial mask further includes a nose piece member having a central section and three edges forming a generally triangular configuration for covering and surrounding the nose of the wearer. The central section of the nose piece member also includes a first opening for connecting to a gas supply; and the nose piece member is adhered along its three edges to the cushioning layer on the gasket member to form a peripheral seal. The central section of the nose piece member has a contoured shape for receiving the wearer's nose therein.

37 Claims, 14 Drawing Sheets

STRAPLESS RESPIRATORY FACIAL MASK FOR CUSTOMIZING TO THE WEARER'S FACE

RELATED APPLICATION

This is a continuation-in-part of application Ser. No. 09/058,437, filed on Apr. 10, 1998.

FIELD OF INVENTION

This invention relates to a kit including a strapless respiratory facial mask for customizing and applying the facial mask to fit the face of many individuals. More particularly, the customized and reusable respiratory mask is sealed tightly to the wearer's facial contours and skin, such that the mask may receive pressurized or non-pressurized gases without leakage of the gases to the surrounding atmosphere. The facial mask can be made to be disposable as well as non-disposable.

BACKGROUND OF THE INVENTION

Respiratory masks, as disclosed in numerous prior art teachings, employ facial straps or head straps in an attempt to bring about a close fit to the wearer's face. There is a need to compress the material of the mask's seal into the wearer's face to make the seal conform to the wearer's facial contours. To accomplish this, the seal cushioning materials of the mask must have sufficient bulk, compressibility and/or sufficient surface area at the periphery of the mask to prevent leakage of the seal. The seal cushioning materials must have flexibility and conformability in order to form a seal to the user's face and also to provide a high degree of comfort when wearing the respiratory mask. In order to provide a good seal of the respiratory mask to the user's face, a high amount of tension must be applied to the frame of the mask, or to the body of the mask, or to the supporting structure of the seal material and this is provided by elastic or cloth straps which may pass over and around the face and head, in order to create a good and sufficient seal. These headgear straps are bulky, uncomfortable, and unaesthetic, but without these elastic straps, a good seal cannot be created by the mask to prevent leakage of the gas being supplied to the respiratory mask.

There are many problems associated with the use of respiratory facial masks. For example, there is the requirement of using head straps or head netting with the mask for maintaining the seal between the respiratory mask and the wearer's facial contours. Elastic straps or stretchable head netting are the primary means of securing the mask to the wearer's face, as these securing means pass over the top of the wearer's head and around the sides of the wearer's head. In many cases these straps and head netting generate considerable tension in order to create and maintain a secure seal on the user's skin. The elastic strap material and the stretchable head netting material are generally uncomfortable when worn, and are typically irritants to the user's facial skin, scalp and hair, particularly if the respiratory mask must be worn for protracted periods of time. In the case of sleep disorder therapy or pulmonary respiratory care where masks are required to be worn for many days or on a permanent basis, such wearing problems are a detriment to successful therapy. Additionally, these head straps and head netting materials are unsightly, bulky and uncomfortable when in use, and the user becomes self-conscious about how it looks and fits, and in some cases, they even refuse to wear the respiratory mask. Again, these wearing problems provide a further detriment to a successful therapy.

Another characteristic problem of prior art respiratory masks, is that the seal for the mask is flexible or the entire respiratory mask is flexible. Such flexible seals are not adequate for producing a tight seal around the user's skin surface area at the periphery of the mask in order to prevent the leakage of gases through the seal. These types of respiratory masks cover the nose and/or mouth area of the patient and are designed in theory to create a continuous seal against the user's face. These masks do not hold their seals because of the individual differences in facial contours and nose dimensions or inadequate sealing materials used for the respiratory mask. Seals have been made from flexible cushioning materials which conform to the face when under compression and tension caused by the elastic straps or stretchable head netting. Cushioning materials include gels, foams, air filled and fluid filled tubes, air bubbles, silicone, urethane, rubber, or other elastomeric materials having recoil and resiliency properties. These aforementioned seal cushioning materials still do not prevent seal leakage of the mask because the adaptability of the material used for the seal is not adequate and the strap tension upon these respiratory masks must be increased to stop the gas leakage. In particular, leakage of pressurized gases around the bridge of the nose causes conjunctivitis. When respiratory masks are uncomfortable, patient's are less likely to comply with wearing the masks for the prescribed amount of time. When the treatment or diagnostic testing for a patient lasts for several hours to several days the patient will only derive a diminished benefit from the foregoing procedures.

It is critical that the retentive forces exerted on the respiratory mask when in use should be limited to the physiological limits of the human skin. A restriction of blood flow in the underlying skin and soft tissue areas has resulted in pain and pressure necrosis among the respiratory masks described in the prior art. This physiological problem occurs in the areas around the bridge of the nose and superior border of the cheek bones where the human face has the greatest facial contour variability and there is less thickness of underlying fat tissue. Many of these prior art masks seem to adapt and seal well in areas where the underlying fat provides a resilient, rebounding cushion which serves to augment the sealing property of the mask's seal cushioning materials. However, in other areas of the face where fat is scant, in order to create a proper and effective sealing action for the respiratory mask, the internal mask pressure must be reduced or strap pressure must be increased. When internal mask pressure is reduced, the maintenance of a specific therapeutic level having an effective positive pressure is lost and the essential therapeutic benefits of the treatment may not be reached to help the patient under treatment. These prior art masks have approached these aforementioned problems by counteracting the forces placed upon the mask by using seal cushioning materials on the outer rim of the mask for cushioning of the face from the compression forces of the headgear straps. This was an attempt to create comfort and reduce elastic strap tension by applying more adaptable and flexible seal materials on the skin contact interface of the mask. Unfortunately, this aforementioned methodology is not routinely successful at eliminating skin trauma, skin irritation and inflammatory reaction to the skin by the patient when wearing these prior art respiratory masks.

There remains a need for a kit to customize a strapless respiratory facial mask to fit the face contours and shapes of various individuals. The respiratory mask should have the capability of being sealed tightly to the wearer's face contours and skin without any skin trauma, irritation, inflammatory reaction, or discomfort to the user's face. In addition, the respiratory mask should have the capability of being sealed tightly to the wearer's facial contours and skin, such that the mask user receives pressurized or non-pressurized gases such as air, oxygen, anesthesia, steam-vapors, and atomized or nebulized medicines without leakage of such substances to the surrounding atmosphere or causing any decreases in gaseous pressure to the wearer. Further, it would be desirable to have a respiratory facial mask and kit which is inexpensive, is simple to customize to the user's face, and has a minimal number of components.

DESCRIPTION OF THE PRIOR ART

Respiratory facial masks of various designs, appearances, styles and materials of construction have been disclosed in the prior art. For example, U.S. Pat. No. 4,467,799 to Steinberg discloses a transparent odor free face mask which covers the mouth and nose area of the face of a wearer. The face mask is made of a thin, formaminous, transparent, thermoplastic and resinous sheet material which has been treated with a transparent bactericide and deodorant. The face mask includes an inverted C-cup shaped housing having a narrow circular flat edging upon which spots of adhesive are applied. The adhesive spots can include rupturable (encapsulated) microballons of pressure-sensitive adhesive or small circular adhesive strips located on the flat edging. This prior art patent does not teach or disclose the structure of the present invention.

U.S. Pat. No. 4,966,140 to Herzberg discloses a protective facial mask constructed of a mask blank having on its opposed edge areas fastening tapes having an adhesive layer for attaching to the user's face area. This prior art patent does not teach or disclose the structure of the present invention.

U.S. Pat. No. 5,647,357 to Barnett et al discloses a respiratory mask facial seal. The respiratory mask includes a seal having an annular member made of liquid urethane material to which a suitable adhesive is applied to the annular seating surface. The annular member is made of material that is sufficiently supplied to conform to the user's facial contours. This prior art patent does not teach or disclose the structure of the present invention.

U.S. Pat. Nos. 2,254,854 and 2,931,356 disclose respiratory masks having continuous cushion sealing that require the use of head straps to maintain the mask to the facial contours of the wearer, so that the sealing effect can take place. These prior art patents do not teach or disclose the structure of the present invention.

None of the prior art patents disclose a kit to customize a strapless respiratory facial mask having viscoelastic thermoset materials or thermoplastic elastomeric materials thereon for fitting and sealing the mask to the facial contours and shapes of various individuals as demonstrated in the present invention.

Accordingly, an object of the present invention is to provide a respiratory facial mask in the form of a kit to customize and apply a strapless respiratory face mask to fit the facial contours and shapes of various individuals when assembled and in operational use.

Another object of the present invention is to provide a respiratory facial mask that has the capability of being sealed tightly to the wearer's facial contours and skin without any skin trauma, skin irritation, or inflammatory reaction to the skin surface when in operational use by the wearer.

Another object of the present invention is to provide a respiratory facial mask that has the capability of being sealed tightly to the wearer's facial contours and skin, such that the mask wearer is able to receive pressurized or non-pressurized gases such as air, pure oxygen, anesthesia, steam-vapors, and atomized or nebulized medicines without leakage of such substances through the seal to the surrounding atmosphere or causing any decreases in gaseous pressure within the mask when in operational use by the wearer.

Another object of the present invention is to provide a respiratory facial mask and kit that is inexpensive, is simple to customize to the user's face; the facial mask can be varied in its intended use by the addition of individual components to the mask; and has a minimal number of component parts in which to assemble for proper operational use by the user.

Another object of the present invention is to provide for a respiratory facial mask that is comfortable to the wearer, has an aesthetically pleasing appearance when worn, and the mask performs as a continuum of the natural skin and being capable of moving with the facial contours and skin of the user.

Another object of the present invention is to provide a respiratory facial mask having a seal cushioning material being made of flexible, viscoelastic thermoset, elastomeric and/or thermoplastic compounds and foams with double-sided tape thereon which is capable of maintaining a seal by being able to move with the facial contours and skin of the wearer, when stretching, pressing or shearing forces are applied to the respiratory mask in operational use by the wearer.

Another object of the present invention is to provide a respiratory facial mask that has the capability of being worn for longer periods of time by a user for diagnostic testing and/or medical treatment in order to achieve a higher success rate of treatment by the user when undergoing such diagnostic and medical procedures.

Another object of the present invention is to provide a respiratory facial mask that has application for use in respiratory therapy, sleep medicine, anesthesia delivery, diagnostic testing, and other medical therapeutic treatments. In addition, the respiratory facial mask can be used for high altitude breathing; military, mining, chemical, metal fabrication and other industrial applications; occupational safety and fire fighting; laboratory procedures; woodworking, metal working, paint spraying and in any environments where dust, pollen, or other air borne contaminants are present.

Another object of the present invention is to provide a strapless respiratory facial mask that requires no compression of the seal against the face so that the wearer is not uncomfortable from the pressing of the seal upon the face.

A further object of the present invention is to provide a respiratory facial mask and kit which can be easily assembled, mass produced in an automated and economical manner, and is readily affordable by the user.

SUMMARY OF THE INVENTION

The present invention provides for a strapless respiratory facial mask for attachment to the wearer's face. The respiratory facial mask includes a moldable laminated gasket member having a cushioning layer and an adhesive layer for engaging the facial contours and skin of the wearer's face; and the gasket member having a central opening for receiving the nose of the wearer. The facial mask further includes a nose piece member having a central section and three edges forming a generally triangular configuration for covering and surrounding the nose of the wearer. The central section of the nose piece member also includes a first opening for connecting to a gas supply; and the nose piece member is adhered along its three edges to the cushioning layer on the gasket member to form a peripheral seal. The central section of the nose piece member has a contoured shape for receiving the wearer's nose therein.

BRIEF DESCRIPTION OF THE DRAWINGS

Further objects, features, and advantages of the present invention will become apparent upon the consideration of the following detailed description of the presently-preferred embodiment when taken in conjunction with the accompanying drawings, wherein.

DETAILED DESCRIPTION OF THE PREFERRED AND ALTERNATE EMBODIMENTS PREFERRED EMBODIMENT 10

Figure 2:
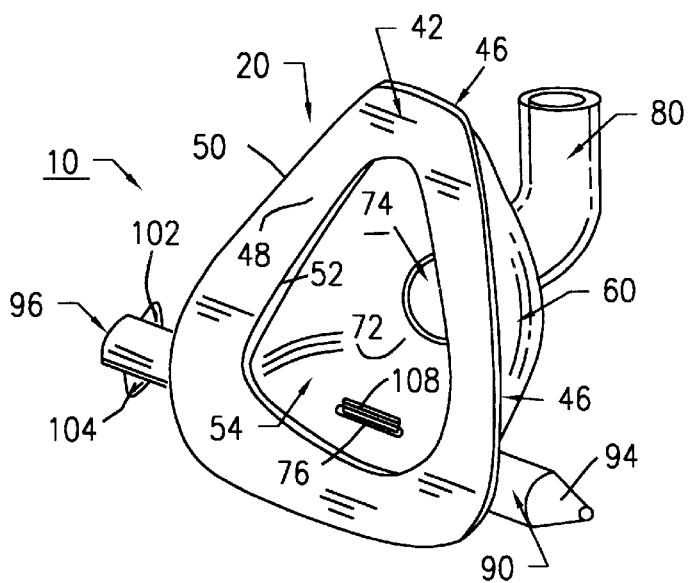
FIG. 2 is a rear perspective view of the strapless respiratory facial mask of the present invention showing the peelable protective covering, the moldable laminated gasket member and the nose piece member.
Figure 3A:
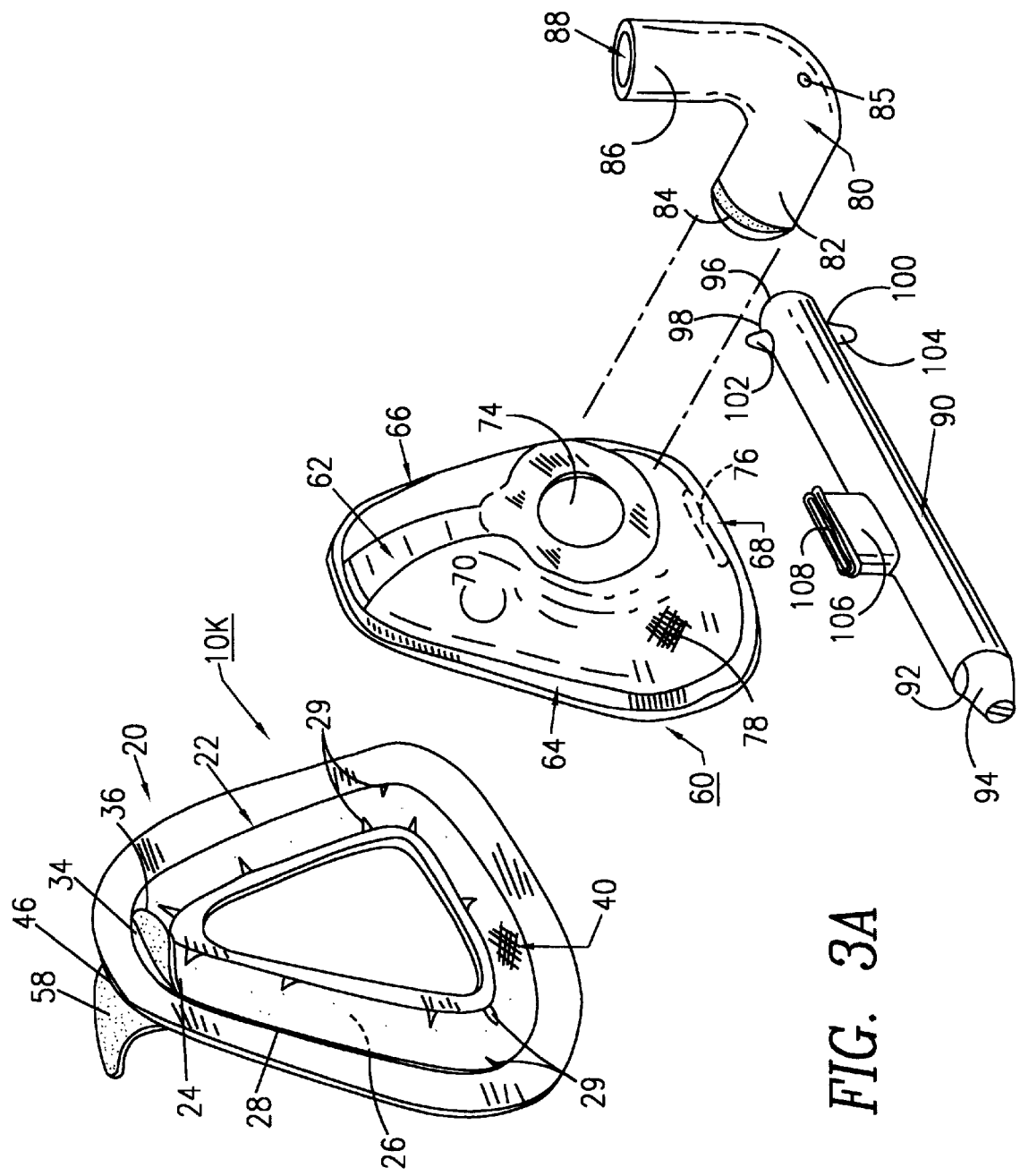
FIG. 3A is an exploded front perspective view of the strapless respiratory facial mask of the present invention showing the component parts of the kit for individual customizing of the facial mask in preparation for operational use.
Figure 3B:
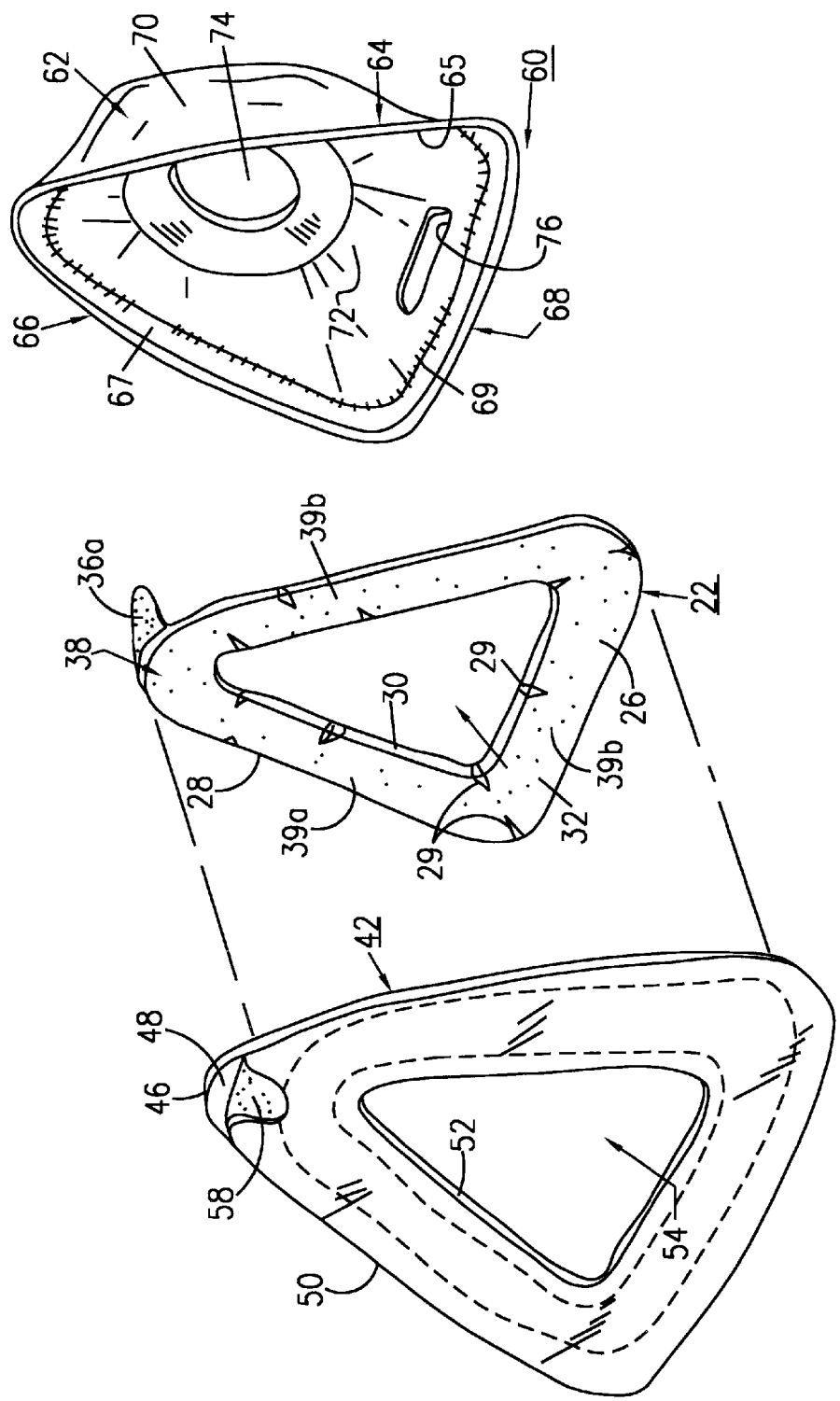
FIG. 3B is an exploded rear perspective view of the strapless respiratory facial mask of the present invention showing the component parts of the kit for individual customizing of the facial mask in preparation for operational use.

The strapless respiratory facial mask 10 and kit 10*k* is used for customizing and applying the facial mask 10 to fit the face 11 of many individuals with a tight seal. The assembled strapless respiratory facial mask 10 and its component parts of the preferred embodiment of the present invention are represented in detail in FIGS. 1, 2 and 4 through 5A, 5B and 6. The kit 10*k* is represented in detail by FIG. 3A and 3B of the drawings. The strapless respiratory facial mask 10 includes a moldable laminated gasket member 20 and a nose piece member 60. The moldable laminated gasket member 20 is used to provide a peripheral sealing area for engaging the facial contours and skin of the wearer's face 11. The moldable laminated gasket member 20 includes a cushioning layer 22 substantially triangular in shape having an exterior surface 24, an interior surface 26, an outer perimeter edge 28, an inner perimeter edge 30, and a center opening 32. Cushioning layer 22 also includes a plurality of release cut-outs 29, as shown in FIGS. 3A and 3B of the drawings, being located and adjacent to the outer and the inner perimeter edges 28 and 30, respectively, of cushioning layer 22. The plurality of release cut-outs 29 allows the laminated gasket member 20 to conform to the facial contours 11 of the wearer's face when in operational use. The exterior surface 24 includes an exterior adhesive layer 34 having a peelable protective covering 36a, and the interior surface 26 includes an interior adhesive layer 38. Interior adhesive layer or inner peripheral sealing section 38 includes a first sealing section 39a, a second sealing section 39b, a third sealing section 39c to engage and match the wearer's facial contours 11.

Adhesive layers 34 and 38 of cushioning layer 22 are selected from the group consisting of double-sided adhesive film, double-sided adhesive tape, pressure-sensitive adhesive, pressure-sensitive glue, pressure-sensitive gel or other adhering materials. Cushioning layer 22 is made from elastic cushioning material 40 selected from the group consisting of elastomeric compounds such as urethanes, polyvinylchloride foam, polytetrafluoroethylene foam, acrylic foam, polyethylene foam, urethane foams, silicone foams, silicones, rubber, neoprene, polystyrene foam and combinations thereof. The peelable protective covering 36a is used for protecting the attaching exterior surface 34 of the cushioning layer 22. The peelable protective covering 36a is made from materials selected from the group consisting of paper, cellophane, polyvinyl chloride (PVC), aluminum foil, polyethylene (PE), Teflon™, silicone tapes, silicone coated paper, plastic film or composites thereof.

The moldable laminated gasket member 20 also includes an adhesive tape layer 42 substantially triangular in shape having an exterior adhesive surface 44, a film layer 46, an interior adhesive surface 48, an outer perimeter edge 50, an inner perimeter edge 52 and a center opening 54. Interior adhesive surface 48 includes an interior peelable protective covering 58. Adhesive surfaces 44 and 48 of adhesive layer 42 are selected from the group consisting of double-sided adhesive film, double-sided adhesive tape, pressure-sensitive glue, pressure-sensitive gel or other adhering materials.

Figure 1:
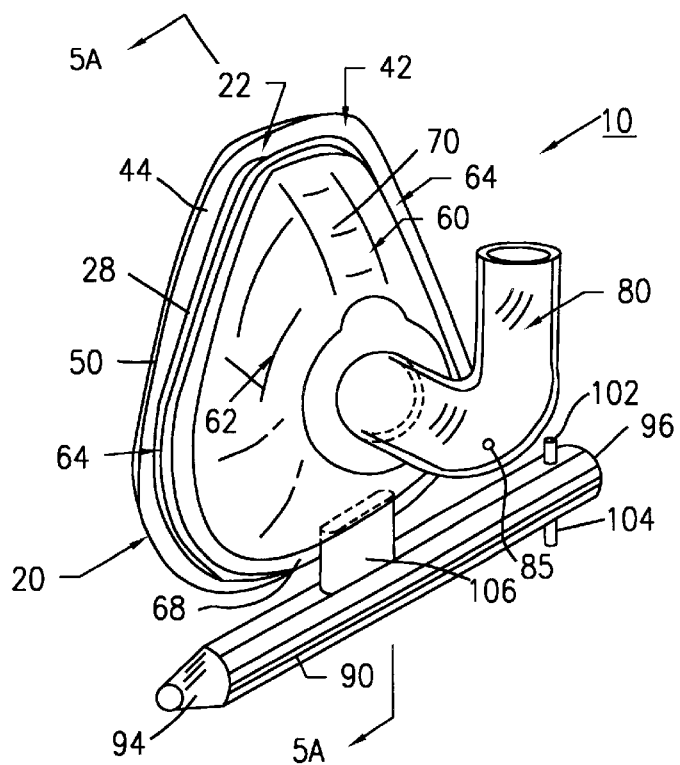
FIG. 1 is a front perspective view of the strapless respiratory facial mask of the preferred embodiment of the present invention showing the moldable laminated gasket member and the nose piece member.

The nose piece member 60 is used for connecting to the rotatable respiratory hose connector 80 and for connecting to the subnasal respiratory hose connector 90 for making connection to a pressurized or non-pressurized gas supply 130 via a first central opening 74 and a second central opening 76, respectively. Nose piece member 60, as shown in FIG. 1, 3A and 3B of the drawings, being substantially triangular in shape including a central section 62 having three peripheral edges 64, 66, and 68, an exterior wall surface 70 and an interior wall surface 72. In addition, central section 62 further includes a first central opening or anterior portal 74 for attachment to the L-shaped, swiveling or rotatable respiratory hose connector 80 or an exhale valve/spring valve 112 for expelling carbon dioxide ($CO_2$) gas out of the facial mask 10 when in use. Connector 80 or exhale valve 112 can be glued into portal 74 or snapped into place for mounting therein. There is also a second central opening or subnasal portal 76 for detachable receiving the subnasal respiratory hose connector 90 therein. The subnasal portal 76 is located directly below and adjacent to the anterior portal 74, as shown in FIGS. 1 and 2 of the drawings. The interior wall surface 72 of central section 62 includes inner surface contact sections or inner sealing section perimeter walls 65, 67 and 69 for attaching to the outer perimeter edge 28 of cushioning layer 22 of gasket 20. The nose piece member 60 is formed of thermoplastic or elastomeric resin materials selected from the group consisting of ethylene vinyl acetate, methyl vinyl acetate, methyl acrylate, polypropylene, polyethylene, ELVAX™, polytetrafluoroethylene resin, urethanes, an acrylic or a carboxylate compound.

The thermoplastic material 78 of choice for the heat moldable nose piece member 60 is ELVAX™ from DuPont Corporation having a durometer reading in the range of 73 to 78. The method of molding the nose piece member 60 to custom fit the anatomy of the face 11 is accomplished by heating the nose piece member 60 with a hair blower until the material 78 is pliable, or alternatively, the nose piece member 60 can be soaked in near boiling/hot water for 15 to 30 seconds and then allowed to cool for a few seconds. The pliable nose piece member 60 is then pressed onto the face 11, and using finger pressure by the practitioner/doctor, the nose piece member 60 is adapted to the bridge 12 of the nose 14, as well as to the cheek areas 13l and 13r of the face 11 (the orbital rim area and the side of the bony nose) and the skin areas contacting the skin surface of the wearer's face 11. The nose piece member 60 is cooled by running cold water onto member 60 for a minute, and member 60 is then dried, such that nose piece member 60 is ready for attaching and adhering to the adhesive layer 42 and cushioning layer 22 of the moldable laminated gasket member 20, thus forming respiratory facial mask 10 of the preferred embodiment 10 of the present invention, as shown in FIGS. 1 and 2 of the drawings. This method allows the respiratory facial mask 10 greater adaptability to fit the mask 10 to a wider range of facial forms and features.

The central section 62 of nose piece member 60 preferable has a width of 7.0 cm, a height of 7.0 cm, a depth of 4.0 cm and a material thickness of 2 mm. The nose piece member 60 being a triangular configuration has measurements wherein the first and second peripheral edges 64 and 66 are 6.5 cm in length and the third peripheral edge 68 is 4.5 cm in width. The first central opening or anterior portal 74 preferably has a diameter of 2.0 cm; and the second central opening or subnasal portal 76 preferably has a width of 1.25 cm and a length of 2.5 cm. The nose piece member 60 preferably has a width of 9.0 cm, a height of 9.0 cm and a material thickness of 2 mm. The inner sealing section perimeter walls 65, 67 and 69 being a triangular configuration has measurements wherein the first and second inner sealing section perimeter walls 65 and 67 are 9.0 cm in length and 1.0 cm in width and the third inner sealing section perimeter wall 69 is 9 cm in length and 1 cm in width. The aforementioned measurements are representative of an adult size facial mask. The facial mask may be manufactured in several sizes to fit different size men, women, children and infants, and also may be varied in thickness, height and width for different medical applications.

The respiratory hose connector 80 has a first end 82 having a snap-in type connection 84 thereon for connecting to the anterior portal 74 and a second end 86 with an opening 88 therein for receiving air or pressurized gases from pumps or pressurized canisters. Hose connector 80 further includes an exit hole 85 for expired gases. The snap-in type connection 84 allows the respiratory hose connector 80 to swivel and rotate within the anterior portal 74, as shown in FIGS. 3A and 5A of the drawings.

Figure 4:
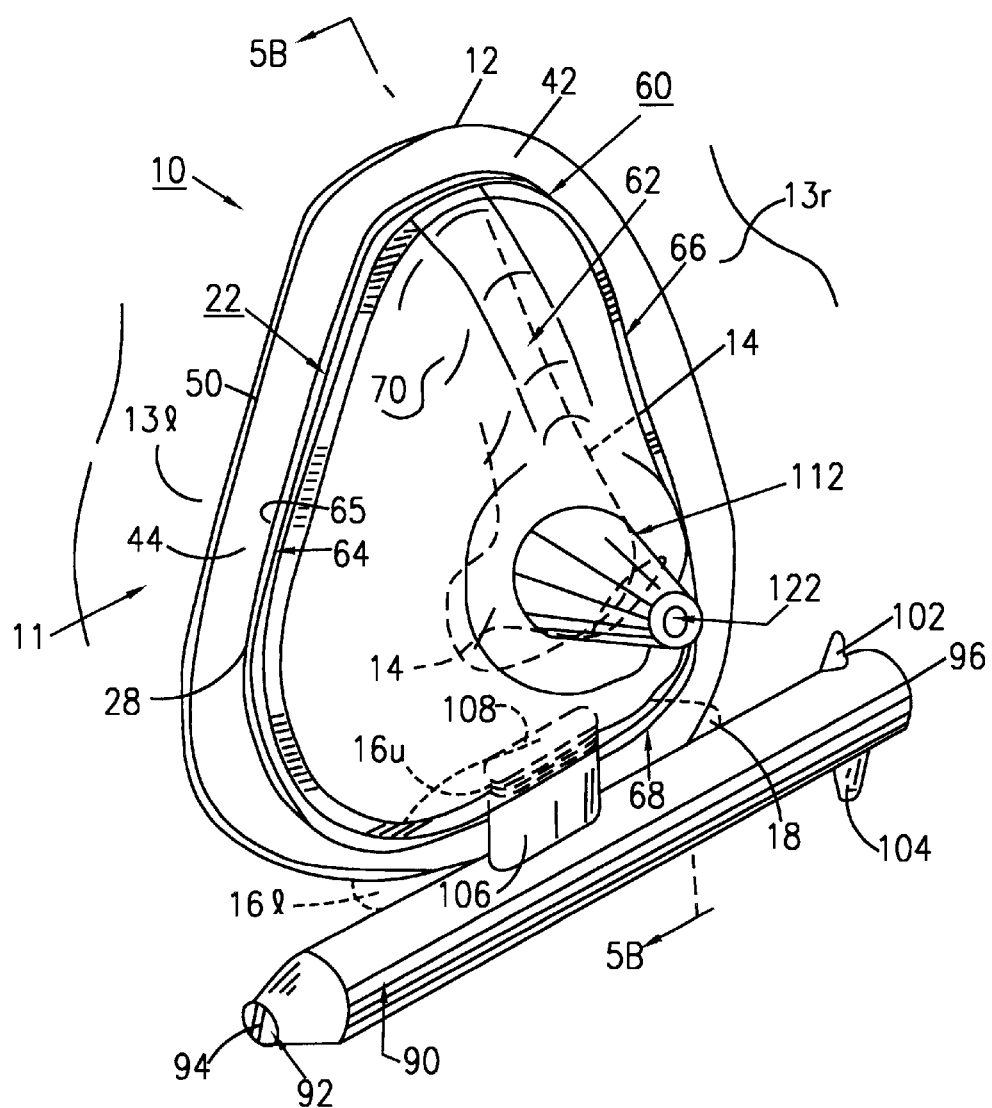
FIG. 4 is an enlarged front perspective view of the strapless respiratory facial mask of the present invention showing the respiratory mask having a moldable laminated gasket member in operational use on the nose and cheek bone areas of a patient.

Alternatively, the respiratory hose connector 80 can be replaced by the use of an exhale spring valve 112 for allowing the expelling and venting of $CO_2$ by the patient through the anterior portal 74. As shown in FIGS. 4 and 5B, spring valve 112 includes a spring component 114, a stop member 116, a plurality of stop arms 118a to 118d, a snap-in type connection 120 thereon for connecting to the anterior portal 74, and a valve opening 122 for venting the expelled $CO_2$ from the patient under a positive pressure mode.

The subnasal respiratory hose connector 90 has an inverted T-shaped tubular configuration. The subnasal respiratory hose connector 90 includes a first end opening 92 having an auxiliary vent component 94 therein; a second end opening 96 for connecting to a gas supply 130; and a pair of diametrically opposed openings 98 and 100 adjacent to the second end opening 96 for receiving a pair of check valves 102 and 104 therein. The subnasal respiratory hose connector 90 further includes an annular component 106 integrally attached and centrally located on the hose connector 90, as shown in FIGS. 1, 2 and 3 of the drawings, and having an annular central opening 108 therein. Annular component 106 also includes a snap-in type connection 110 for alignment and connection to the subnasal portal 76, and valve 112 snaps into anterior portal 74.

SECOND EMBODIMENT 200

The strapless respiratory facial mask 200 and kit 200k is used for customizing and applying the facial mask 200 to fit the face 11 of many individuals with a tight seal. The assembled strapless respiratory facial mask 200 and its component parts of the second embodiment of the present invention are represented in detail in FIGS. 7, 8, 10 through 12 of the drawings. The kit 200k is represented in detail by FIG. 9 of the drawings. The strapless respiratory facial mask 200 includes a moldable mask housing 220 and a pair of first and second lateral cheek flaps 250 and 260, as shown in FIGS. 7, 8, 9 and 10 of the drawings.

Mask housing 220 includes a central section 222 being substantially triangular in shape having a first perimeter lip 224, a second perimeter lip 226 and a third perimeter lip 228 integrally attached thereto. Perimeter lips 224, 226 and 228 are also substantially formed in a triangular plane, and having an apex area section 240 formed from the first and second perimeter lips 224 and 226 for moldably conforming to the upper bridge area 12 of the nose 14 of the user's face 11. Perimeter lip 228 is used to provide a peripheral sealing area for moldably conforming to the upper lip area 16u or bottom lip area 16l of the mouth 18 of the wearer's facial contours 11. Central section 222 includes an exterior wall surface 230 and an interior wall surface 232 and a center opening 234 for receiving therein a rotatable respiratory hose connector (swivel elbow connector) 270. The central opening or anterior portal 234 for attachment to the L-shaped, swiveling or rotatable respiratory hose connector 270 or an exhale valve/spring valve 112 for expelling carbon dioxide ($CO_2$) gas out of the facial mask 200 when in use. Connector 270 or exhale valve 112 can be glued into portal 234 or snapped into place for mounting therein. There is also a second optional central opening or subnasal portal (similar to that of the preferred embodiment) for detachable receiving the subnasal respiratory hose connector 90 of the preferred embodiment therein. The subnasal portal would be located directly below and adjacent to the anterior portal 234, similar to that of the preferred embodiment, as depicted in FIG. 2 of the drawings. Mask housing 220 is formed from a plastic resin, viscoelastic thermoset compounds, a thermoplastic or an elastomeric resin material 238 selected from, for example, the group consisting of ethyl vinyl acetate, methyl vinyl acetate, methyl acrylate, polyethylene, polypropylene, ethylene, vinyl acetate, ELVAX™, polytetrafluoroethylene, silicone, Sorbothane™, polystyrene, urethanes, an acrylic or a carboxylate compound.

Figure 8:
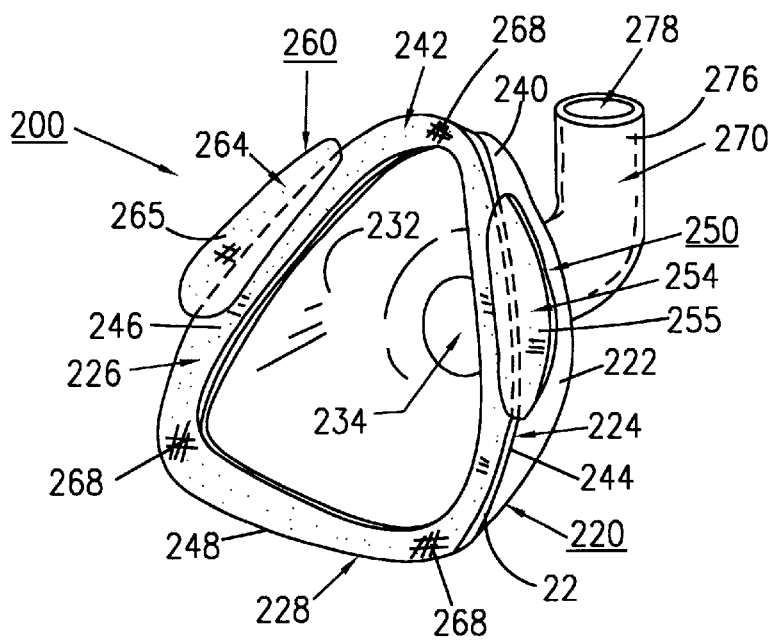
FIG. 8 is a rear perspective view of the strapless respiratory facial mask of the present invention showing the peelable protective covering on the perimeter lips having an adhesive surface thereon and the central section having a center opening therein.
Figure 9:
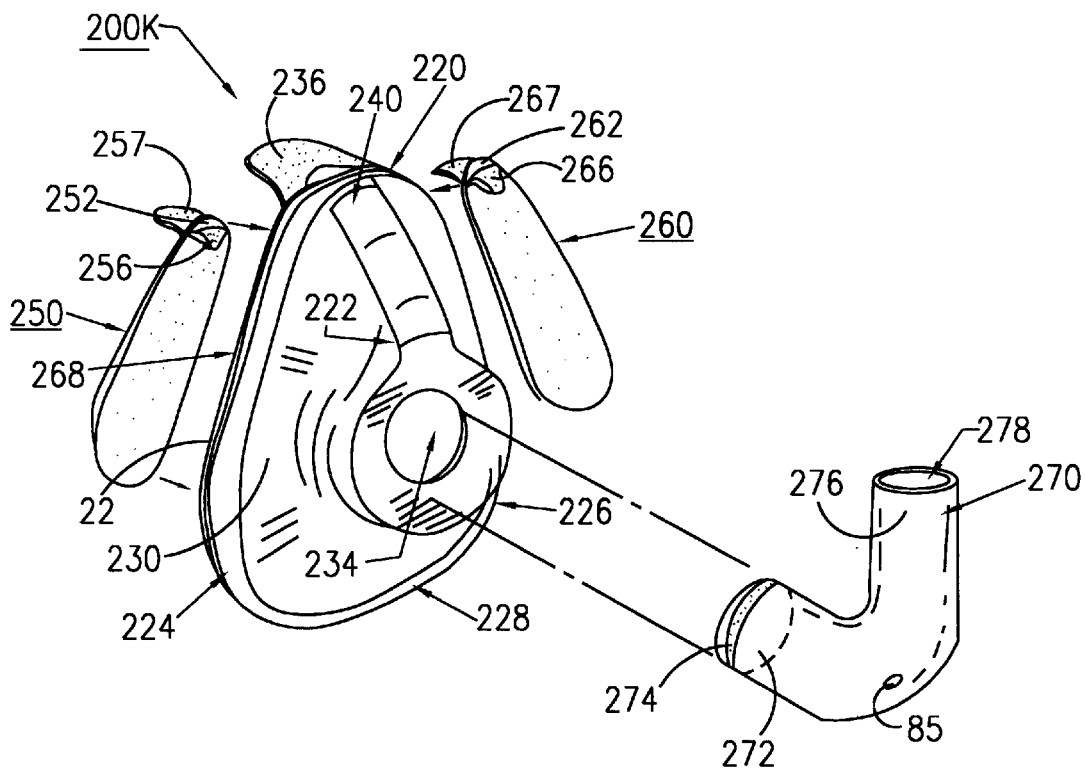
FIG. 9 is an exploded perspective view of the strapless respiratory facial mask of the present invention showing the component parts of the kit for individual customizing of the facial mask in preparation for operational use.

The first, second and third perimeter lips 224, 226 and 228 include inner first, second and third peripheral sealing adhesive lips 244, 246 and 248, respectively, for forming a triangular shaped peripheral adhesive sealing area 242 for engaging and attaching to a gasket cushioning member 22 (as shown in the preferred embodiment). Gasket cushioning member 22 is used for engaging the facial contours of the nose 14 and mouth 18 areas and skin of the wearer's face 11. This peripheral adhesive sealing (border) area 242 may be augmented in its adhesion to the cushioning gasket member 22 by treating with chemical means or plasma treatment means such that a pressure sensitive adhesive material 268 is directly applied and infused to each of the inner first, second and third peripheral sealing adhesive lips 244, 246 and 248 of the adhesive sealing/border area 242 of mask housing 220, as depicted in FIGS. 8 and 9 of the drawings. Peripheral adhesive sealing area 242 is made from an adhesive material selected from the group consisting of pressure-sensitive adhesive, pressure-sensitive glue, pressure-sensitive gel or other adhering materials. The peripheral sealing/border area 242 includes an interior peelable protective covering 236 attached thereto being substantially triangular in shape, as depicted in FIGS. 8 and 9 of the drawings. The peelable protective covering 236 is made from materials selected from the group consisting of paper, cellophane, polyvinyl chloride (PVC), aluminum foil, polyethylene (PE), Teflon™, silicone tapes, gels, plastic film or composites thereof. Mask housing 220 has the ability to be customized by trimming the perimeter lips 224, 226 and 228 or by adding the first and/or second lateral cheek flaps 250 or 260 to the first and second perimeter lips 224 or 226 prior to adhering to the patient's face 11.

First lateral cheek flap 250 includes an exterior wall surface 252 having an exterior adhesive surface 253, and includes an interior wall surface 254 having an interior adhesive surface 255. Adhesive surfaces 253 and 255 each have an exterior and an interior peelable protective covering 256 and 257, respectively thereon. Second lateral cheek flap 260 includes an exterior wall surface 262 having an exterior adhesive surface 263, and includes an interior wall surface 264 having an interior adhesive surface 265. Adhesive surfaces 263 and 265 each have an exterior and an interior peelable protective covering 266 and 267, respectively, thereon. First and second lateral cheek flaps 250 and 260 are made from elastic cushioning material 210 selected from the group consisting of elastomeric compounds such as urethanes, polyvinylchloride foam, polytetrafluoroethylene foam, acrylic foam, polystyrene foam, polyethylene foam, urethane foams, Sorbothane™, silicones, silicone foams, rubber, neoprene, and combinations thereof. Adhesive surfaces 253, 255, 263 and 265 of first and second lateral cheek flaps 250 and 260, respectively, are made from adhesive materials or adhesive material layers 268 selected from the group consisting of double-sided film, double-sided adhesive tape, pressure-sensitive adhesive, pressure-sensitive glue, pressure-sensitive gel or other adhering materials. The peelable protective coverings 256, 257, 266 and 267 are used for protecting the attaching adhesive surfaces 253, 255, 263 and 265, respectively, of the first and second lateral cheek flaps 250 and 260, respectively. The peelable protective coverings 256, 257, 266 and 267 are made from materials selected from the group consisting of paper, cellophane, polyvinyl chloride (PVC), aluminum foil, polyethylene (PE), Teflon™, silicone coated paper, plastic film or composites thereof.

Additionally, the first and/or second lateral cheek flaps 250 and 260 can also be customized by trimming the width and/or length of the cheek flaps 250 and/or 260 in order to provide more effective peripheral sealing areas to the wearer's cheek bone areas 13*l* and 13*r* for tightly sealing the mask 200 to the contours and skin of the wearer's face 11 and for preventing the leakage of gas therefrom.

The central section 222 of mask housing 220 being a triangular configuration has measurements wherein the width of 5.5 cm, a height of 6.5 cm, a depth of 3.0 cm and a material thickness of 2 mm. The first, second and third perimeter lips 224, 226 and 228 of central section 222 are 9.0 cm in length and are 4.5 cm in width. The first central opening or anterior portal 34 preferably has a diameter of 2.0 cm; and the second central opening or subnasal portal (being optional—not shown) preferably has a width of 1.25 cm and a length of 2.5 cm, similar to preferred embodiment 10. The peripheral sealing section 242 of mask housing 220 preferably has a width of 9.0 cm, a height of 9.0 cm and a material thickness of 5 mm. The peripheral sealing section 242 being a triangular configuration has measurements wherein the first, second and third peripheral sealing adhesive lips 244, 246 and 248 are 9.0 cm in length and 4.5 cm in width. The lateral cheek flaps 250 and 260 preferably have a width of 1.5 cm, a length of 5.0 cm and a material thickness of 5 mm. The aforementioned measurements are representative of an adult size facial mask. The facial mask may be manufactured in several sizes to fit different size men, women, children and infants, and also may be varied in thickness, height and width for different medical applications.

Figure 12:
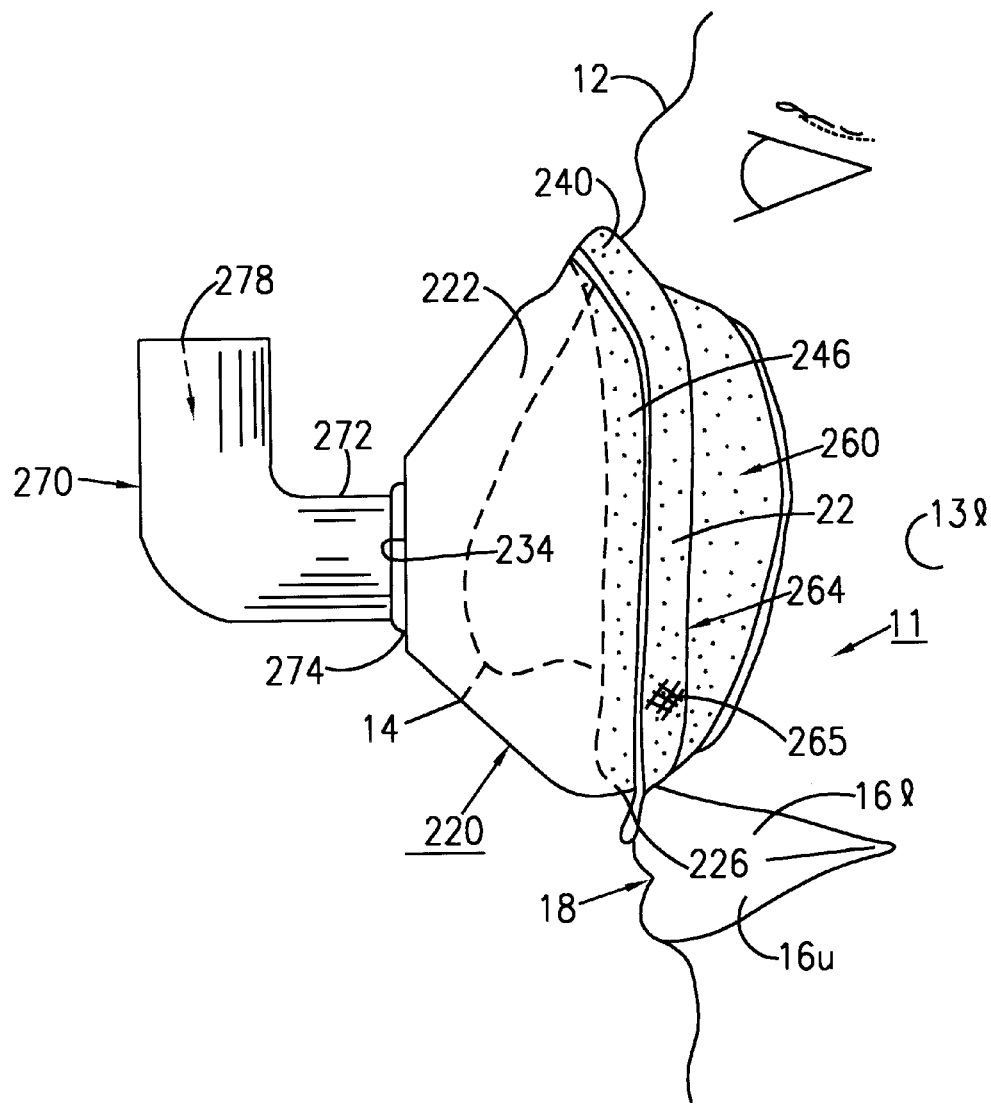
FIG. 12 is a side elevational view of the strapless respiratory facial mask of the present invention showing the facial mask in operational use such that there is an increased space for a larger nose and wider cheek bones when using the cheek lateral flaps and lip flap of the present invention.
Figure 13:
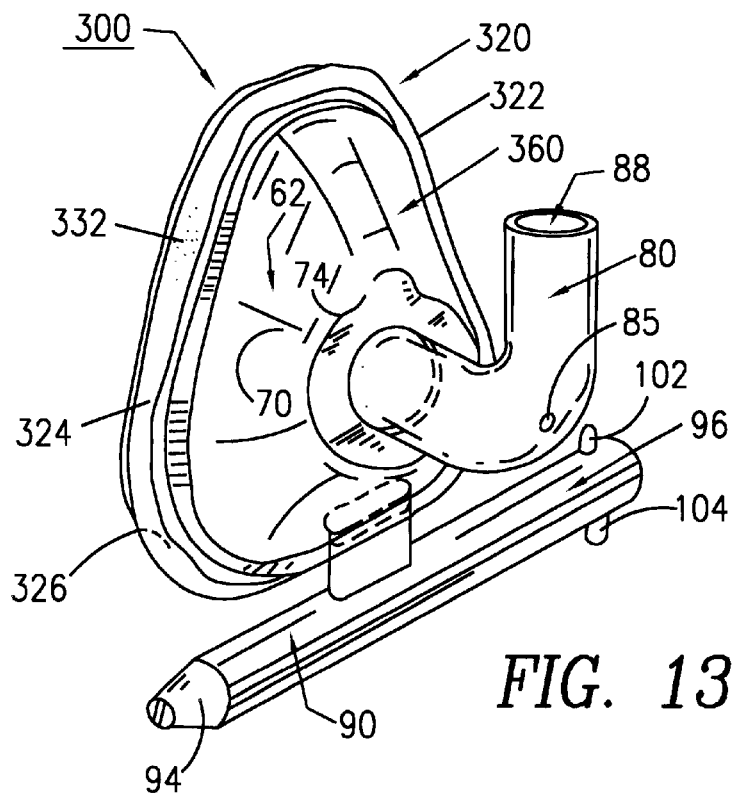
FIG. 13 is a front perspective view of the strapless respiratory facial mask of the second alternate embodiment of the present invention showing the facial respiratory mask and its major components contained therein.

The respiratory hose connector 270 has a first end 272 having a snap-in type connection 274 thereon for connecting to the anterior portal 234 and a second end 276 with an opening 278 therein for receiving air or pressurized gases from pumps or pressurized canisters. The snap-in type connection 274 allows the respiratory hose connector 270 to swivel and rotate within the anterior portal 234, as shown in FIGS. 12 and 13A of the drawings.

Figure 10:
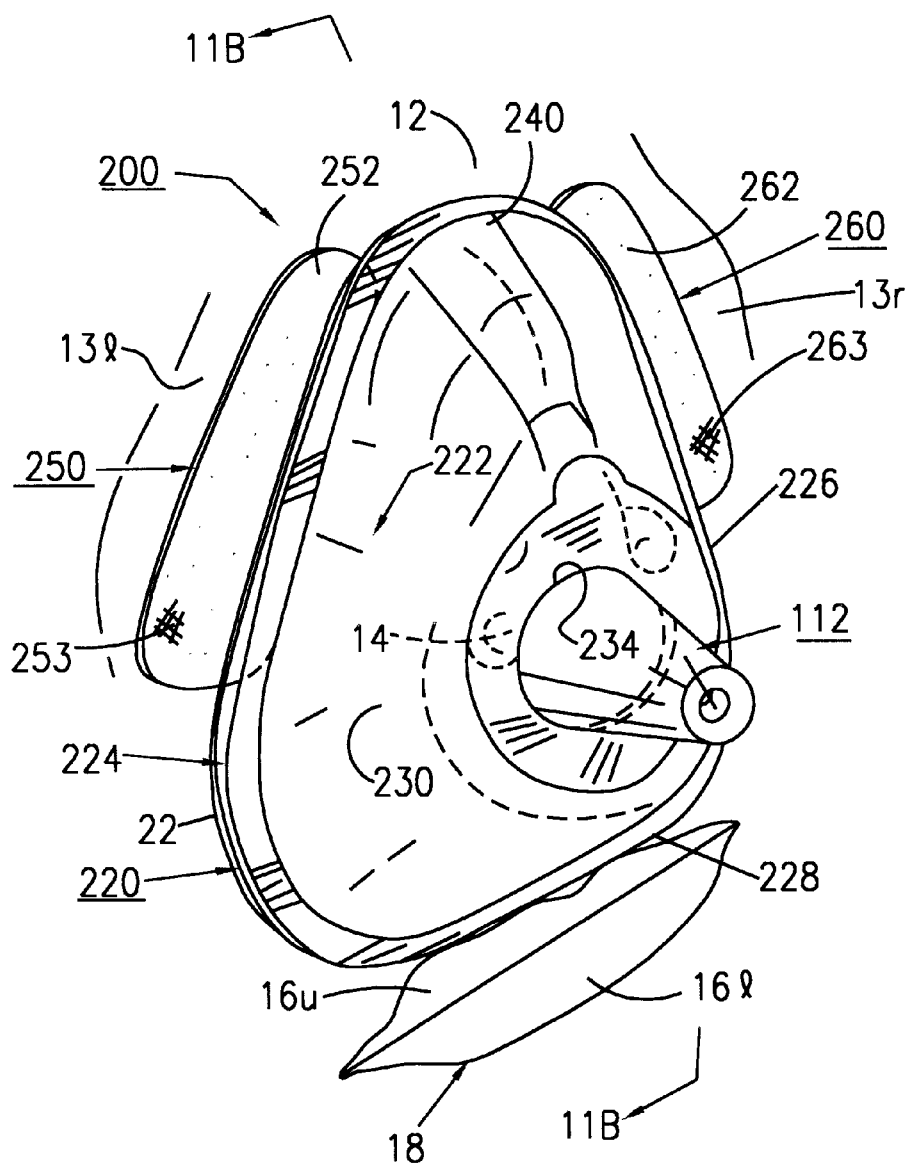
FIG. 10 is an enlarged front perspective view of the strapless respiratory facial mask of the present invention showing the respiratory mask and its component parts in operational use on the nose and cheek bone areas of a patient.
Figure 11A:
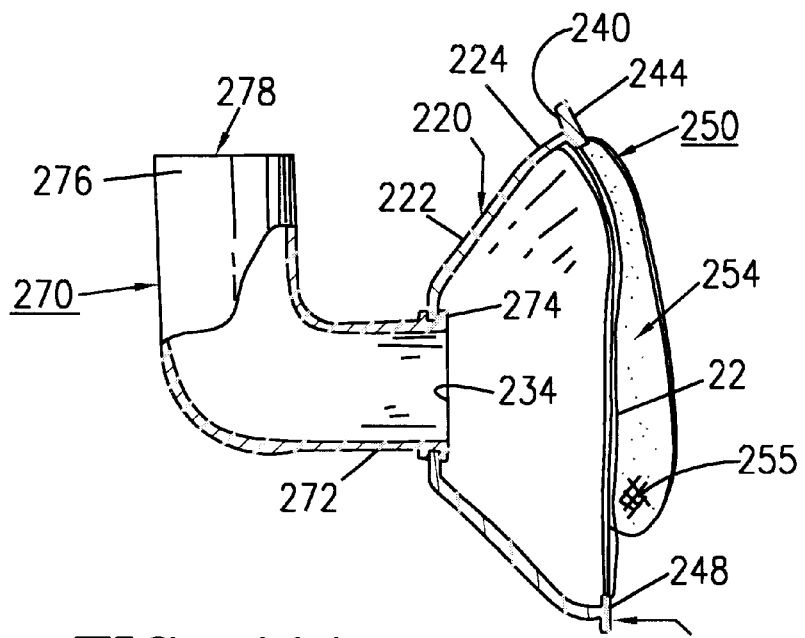
FIG. 11A is a cross-sectional view of the strapless respiratory facial mask of the present invention taken along lines 11A—11A of FIG. 7 showing the anterior portal having a respiratory hose connector therein, the nose component, the peripheral seal, perimeter lips, and the peelable protective covering.
Figure 11B:
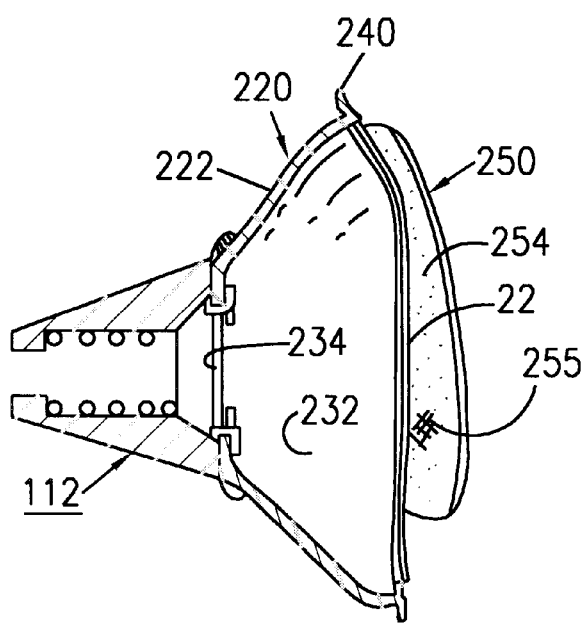
FIG. 11B is a cross-sectional view of the strapless respiratory facial mask of the present invention taken along lines 11B—11B of FIG. 19 showing the interior portal having an exhale spring valve therein, the nose component, the peripheral seal cushioning material and peelable protective covering.

Alternatively, the respiratory hose connector 270 can be replaced by the use of an exhale spring valve 112 for allowing the expelling and venting of $CO_2$ by the patient through the anterior portal 270. As shown in FIGS. 10 and 11B, spring valve 112 includes a spring component 114, a stop member 116, a plurality of stop arms 118*a* and 118*d*, a snap-in type connection 110 thereon for connecting to the anterior portal 74, and a valve opening 122 for venting the expelled $CO_2$ from the patient under a positive pressure mode.

THIRD EMBODIMENT 300

Figure 14:
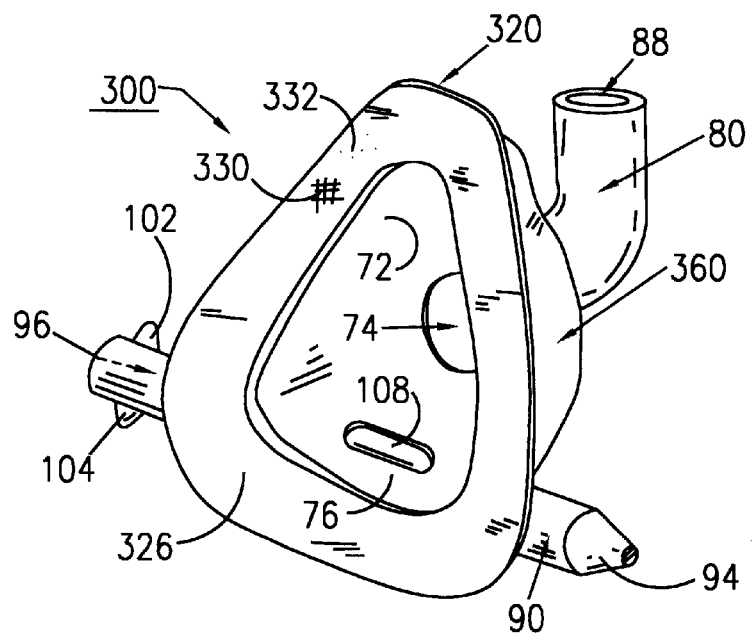
FIG. 14 is a rear perspective view of the strapless respiratory facial mask of the present invention showing the peelable protective covering on the perimeter lips having an adhesive surface thereon and the central section having a center opening therein.
Figure 15:
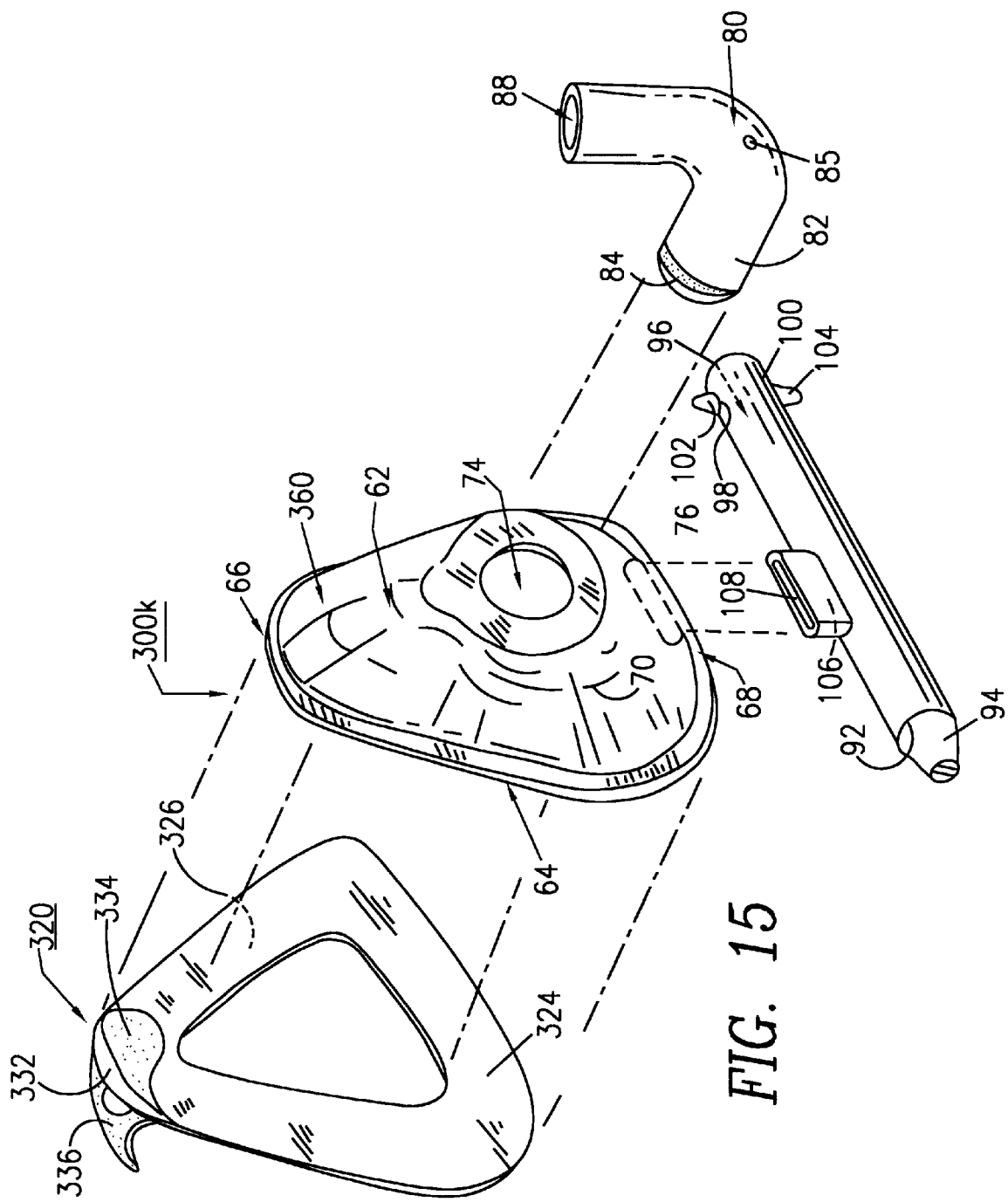
FIG. 15 is an exploded perspective view of the strapless respiratory facial mask of the present invention showing the component parts of the kit for individual customizing of the facial mask in preparation for operational use.

The strapless respiratory facial mask 300 and kit 300*k* is used for customizing and applying the facial mask 300 to fit the face 11 of many individuals with a tight seal. The assembled strapless respiratory facial mask 300 and its component parts of the third embodiment of the present invention are represented in detail in FIGS. 13 to 15 of the drawings. All aspects of the third embodiment 300 of the respiratory facial mask are exactly the same as the preferred embodiment of the respiratory facial mask 10, except for gasket member 320 being a single layer 322 of elastomeric material 330 (similar to the cushioning layer 22 of laminated gasket member 20 of the preferred embodiment) having an adhesive material 332 on each exterior and interior wall surface 324 and 326, respectively, of gasket member 320. The adhesive tape layer 42 of laminated gasket member 20 has been eliminated from this gasket member 320 of the third embodiment. In addition, adhesive material 332 on each wall surface 324 and 326 of gasket member further includes an exterior and an interior peelable protective covering 334 and 336, respectively. In operation, gasket member 320 is adhered to the face 11 of the wearer and the nose piece member 360 is adhered to gasket member 320, similar to that of the preferred embodiment 10 of the present invention.

FOURTH EMBODIMENT 400

Figure 16:
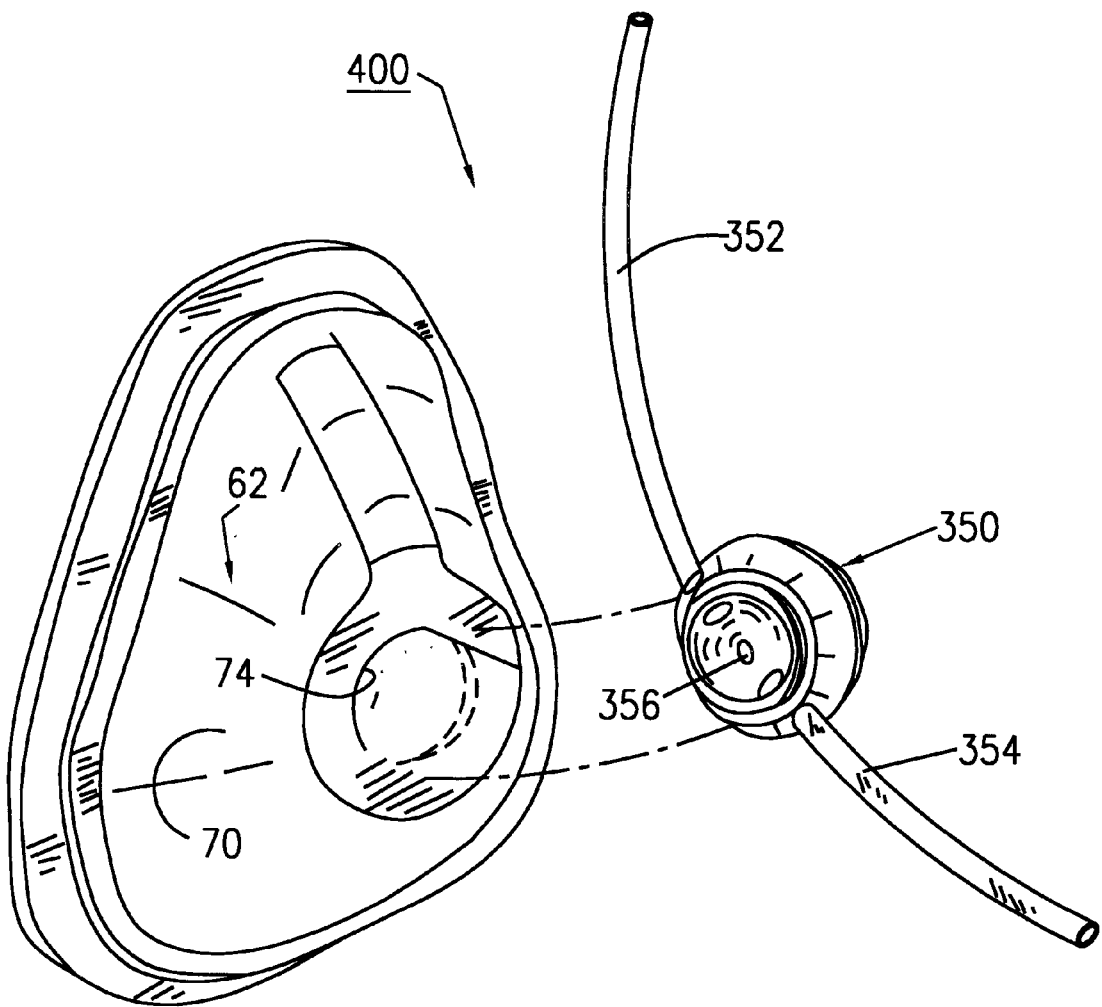
FIG. 16 is a front perspective view of the strapless respiratory facial mask of the third alternate embodiment of the present invention showing a respiratory gas and/or anesthesia swivel hose connector with a pair of gas tubes attached thereto being connected to the nose member.

The strapless respiratory facial mask 400 is used for customizing and applying the facial mask 400 to fit the face 11 of many individuals with a tight seal. The assembled strapless respiratory facial mask 400 and its component parts of the fourth embodiment of the present invention are represented in detail in FIGS. 16 of the drawings. All aspects of the fourth embodiment 400 of the respiratory facial mask are exactly the same as the third embodiment of the respiratory facial mask 300, except for a respiratory gas and/or anesthesia swivel hose connector 350 having a pair of gas tubes 352 and 354 attached thereon which replaces hose connector 80. Hose connector 350 further includes an exit hole 356 for expired air.

OPERATION OF THE PRESENT INVENTION PREFERRED EMBODIMENT 10

In operation, the kit 10*k* of the preferred embodiment of the present invention, as shown in FIGS. 1 to 6 of the drawings, provides a method of customizing and applying a respiratory facial mask 10 to the wearer's face 11 with a tight seal without the need for head straps or head netting. This method of customizing and applying may be applied to nasal masks, as in the present invention, as well as oral-nasal masks which cover the entire mouth and nose area. The respiratory facial mask 10 includes an anterior portal 74 and a subnasal portal 76, instead of the usual one opening in prior art respiratory masks, for increased respiratory assistance to the user such that the two portals/openings 74 and 76 can be used simultaneously or individually. The central section 62 and the inner sealing section perimeter walls 65, 67 and 69 of nose piece member 60 are customized to each individual face 11 and the strapless respiratory facial mask 10 is assembled such that the mask 10 is tailor made for specific medical or non-medical therapy to be administered from an intermittent or continuous gas supply 130. The thermoplastic material 78 of choice for the heat moldable nose piece member 60 is ELVAX™ from DuPont Corporation having a durometer reading in the range of 73 to 78.

A step-by-step process is utilized for assembling the mask kit 10*k* and applying it to the user's facial contours and skin. The first step is the method of molding the nose piece member 60 to custom fit the anatomy of the face 11. This molding step is accomplished by heating the nose piece member 60 with a hair blower until the material 78 is pliable, or alternatively, the nose piece member 60 can be soaked in near boiling/hot water for 15 to 30 seconds and then allowed to cool for a few seconds. The pliable nose piece member 60 is then pressed onto the face 11, and using finger pressure by the practitioner/doctor, the nose piece member 60 is adapted to the bridge area 12 of the nose 14, as well as to the cheek areas 13*f* and 13*r* of the face 11 and the skin areas contacting the skin surface of the wearer's face 11. The nose piece member 60 is cooled by running cold water onto member 60 for a few seconds, and member 60 is then dried, such that nose piece member 60 is subsequently ready for attaching and adhering in a latter step to the adhesive layer 42 and cushioning layer 22 of the moldable laminated gasket member 20, thus forming respiratory facial mask 10 of the preferred embodiment 10 of the present invention, as shown in FIGS. 1 and 2 of the drawings. This method allows the respiratory facial mask 10 greater adaptability to fit the mask 10 to a wider range of facial forms and features.

The second step is the trimming of one or more of the first, second and/or third sealing sections 39a, 39b and 39c of the inner peripheral sealing section 38 of the cushion layer 22 from the moldable laminated gasket member 20 in order to match the person's facial contours 11.

The next step is the removing of the interior peelable protective covering from the first, second and third sealing sections 39a, 39b and 39c of the inner peripheral sealing section 38 in preparation for adhering the peripheral sealing section 38 of the moldable laminated gasket member 20 to the wearer's face 11.

The fourth step is the adhering of the first, second and third sealing sections 39a, 39b and 39c of the inner peripheral sealing section 38 of the laminated gasket member 20 by pressing gasket member 20 with finger pressure by the practitioner/doctor to the person's facial contours 11 and skin in order to obtain an airtight seal between the moldable laminated gasket member 20 of mask 10 and the person's face 10.

The next step is the molding of the laminated gasket member 20 to a person's facial contours 11, and conforming the first and second sealing sections 39a and 39b of the gasket member 20 to the bridge area 12 of the nose and to the cheek bone areas 13l and 13r of the wearer's face 11, and conforming the third sealing section 39c on the gasket member 20 to the upper lip area 16u or to the lower lip area 16l of the person's mouth 18 to obtain a tight fit between the laminated gasket member 20 and the person's face 11.

Figure 5:
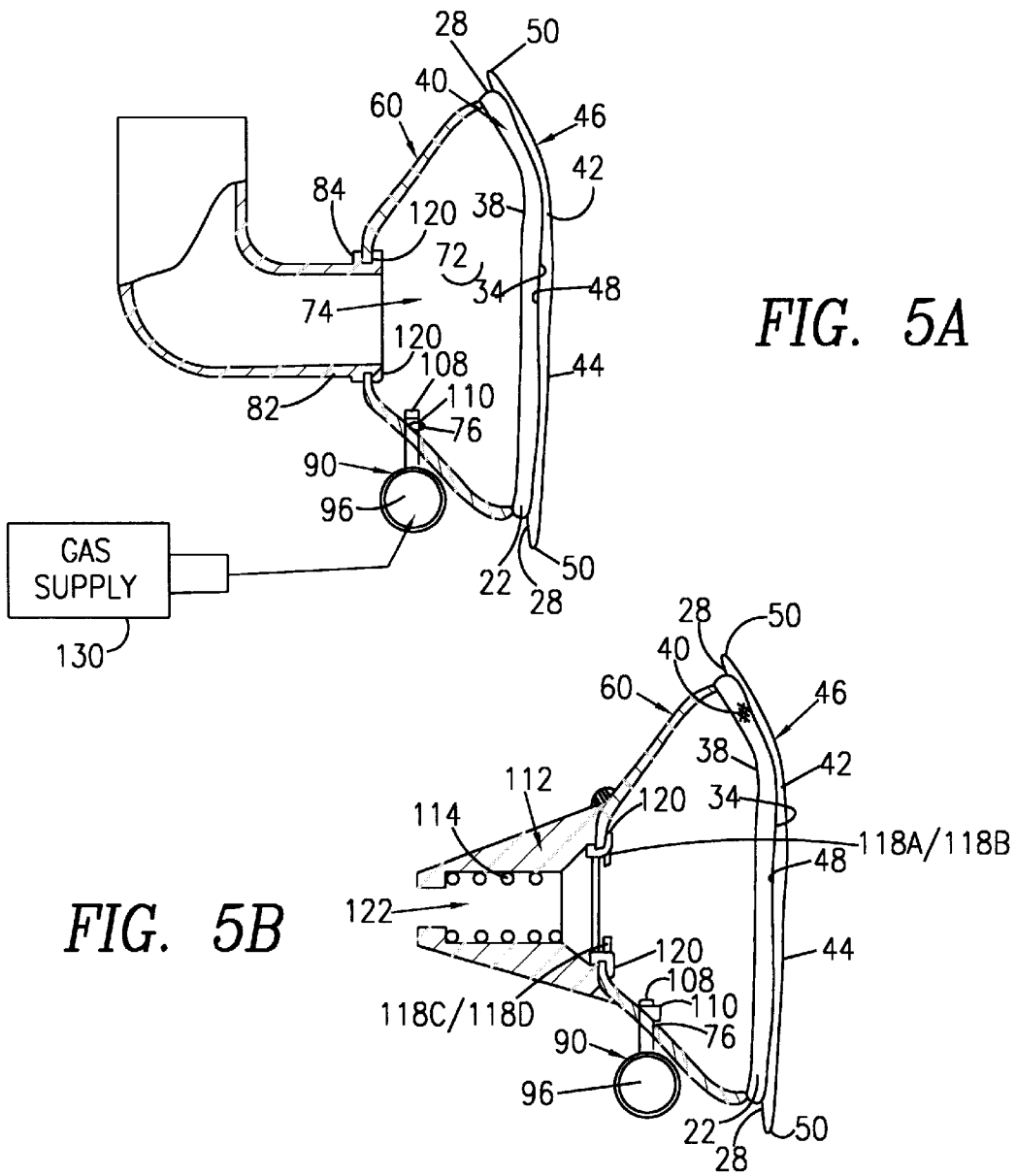
FIG. 5A is a cross-sectional view of the strapless respiratory facial mask of the present invention taken along lines 5A—5A of FIG. 1 showing the anterior portal having a respiratory hose connector therein, the subnasal portal having a subnasal respiratory hose connector with a check valve therein, the nose piece member, the moldable laminated gasket member, and the peelable protective covering.
FIG. 5B is a cross-sectional view of the strapless respiratory facial mask of the present invention taken along lines 5B—5B of FIG. 4 showing the anterior portal having an exhale spring valve therein, the subnasal portal having a subnasal respiratory hose connector with a check valve therein, the nose piece member, the moldable laminated gasket member and the peelable protective covering.
Figure 6:
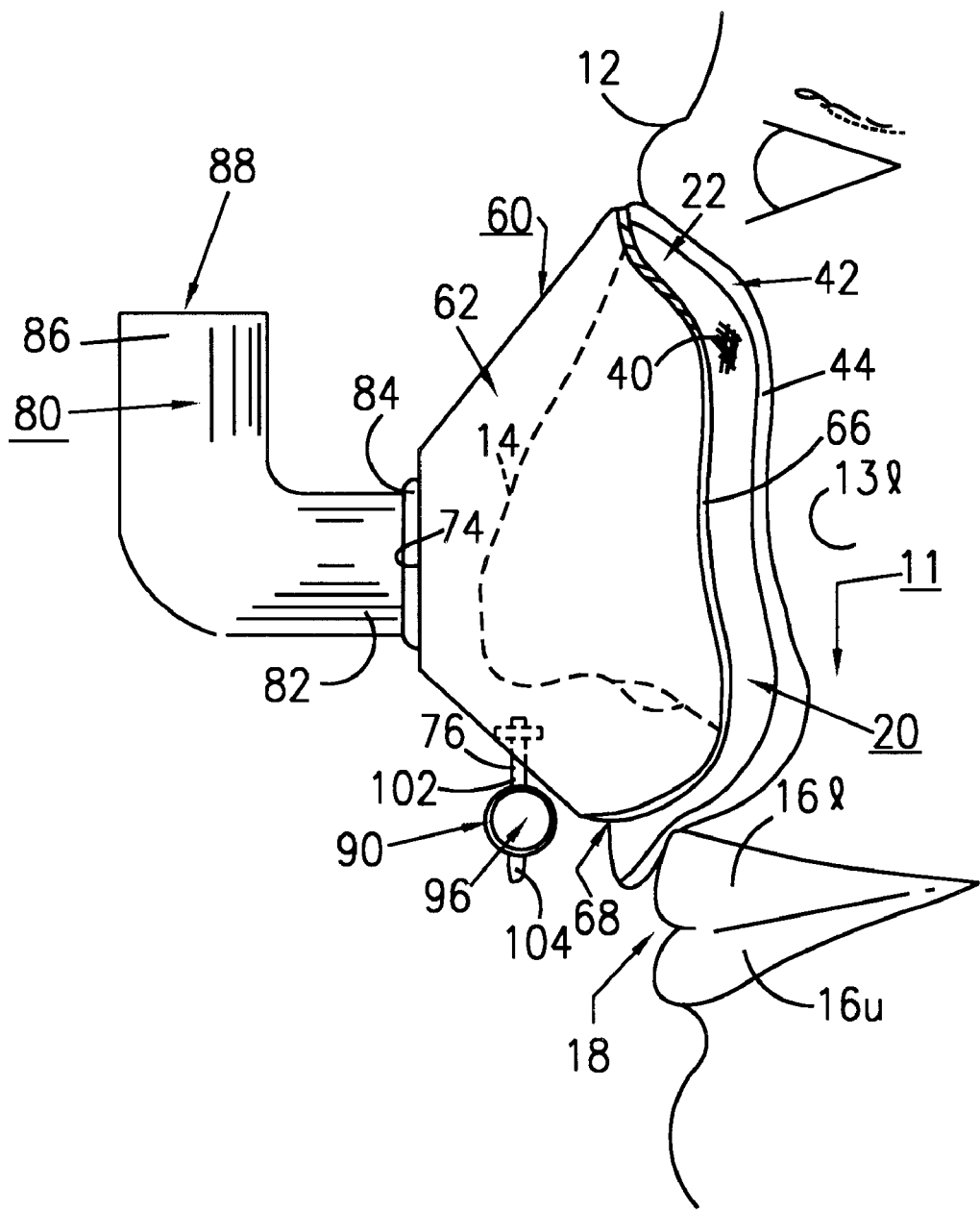
FIG. 6 is a side elevational view of the strapless respiratory facial mask of the present invention showing the facial mask in operational use such that there is an increased space for a larger nose and wider cheek bones when using the present invention.
Figure 7:
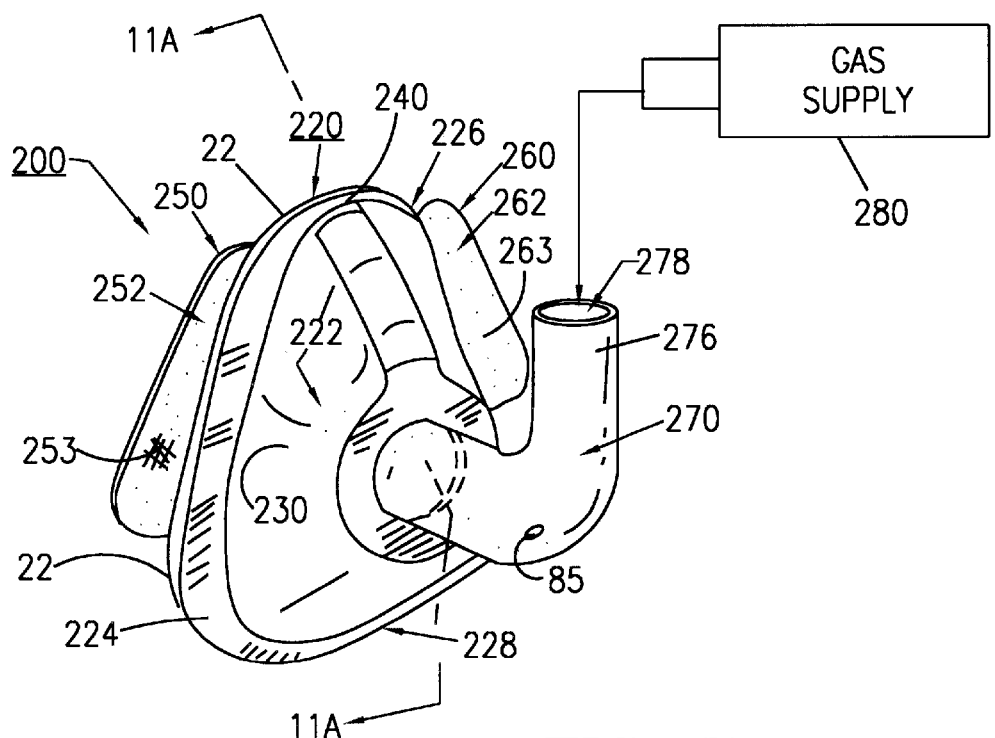
FIG. 7 is a front perspective view of the strapless respiratory facial mask of the first alternate embodiment of the present invention showing the facial respiratory mask and its major components contained therein.

The following step is the adhering of the molded nose piece member 60 to the molded laminated gasket member 20 to form a peripheral airtight seal between the nose piece member 60 and the laminated gasket member 20 to form an overall airtight seal between the respiratory facial mask 10 and the wearer's facial contours 11, as shown in FIGS. 4 to 6 of the drawings.

The next step is the connecting of the rotatable respiratory hose connector 80 to the first central opening 74 for expelling carbon dioxide [$CO_2$] gas out of the facial mask 10 when in use.

The last step is the connecting of the subnasal respiratory hose connector 90 to the second central opening 76 for making connection to a pressurized or non-pressurized gas supply 130 in order to provide respiratory therapy of air or pure oxygen to the patient.

ALTERNATE EMBODIMENT 200

In operation, the kit 200k of the alternate embodiment of the present invention, as shown in FIGS. 9 to 12 of the drawings, provides a method of customizing and applying a respiratory facial mask 200 to the wearer's face 11 with a tight seal without the need for head straps or head netting. This method of customizing and applying may be applied to nasal masks, as in the present invention, as well as oral-nasal masks which cover the entire mouth and nose area. The respiratory facial mask 10 includes an anterior portal and an optional subnasal portal (not shown) for increased respiratory assistance to the user such that the two portals/openings can be used simultaneously or individually. The central section 222 and the peripheral adhesive sealing section area 242 of mask housing 220 are customized to each individual face 11 and the strapless respiratory facial mask 200 is assembled such that the mask 200 is tailor made for specific medical or non-medical therapy to be administered from an intermittent or continuous gas supply 280. The thermoplastic material 238 of choice for the heat moldable mask housing 220 is a ELVAX™ resin from DuPont Corporation having a medium durometer reading in the range of 73 to 78. A pliable non-heat moldable alternative is Sorbothane™ or Teflon™ resin in the low durometer range of 40 to 65.

A step-by-step process is utilized for assembling the mask kit 200k and applying it to the user's facial contours and skin. The first step is trimming one or more of the first, second and/or third perimeter lips 224, 226 and/or 228 of mask housing 220, if necessary, to match the person's facial contours 11, as depicted in FIGS. 10 through 12 of the drawings.

The second step is trimming one or more of the first and second lateral cheek flaps 250 and 260 to match the cheek bone areas 13l and 13r of the person's facial contours 11.

The next step is the molding of the first, second and third perimeter lips 224, 226, 228 and gasket 22 to a person's facial contours and conforming the first and second perimeter lips 224 and 226 to the upper bridge area 12 of the person's nose 14, being conformed to the sides of the bony nose and the orbital rim area, and conforming the third perimeter lip 228 to the upper lip area 16u or to the lower lip area 16l of the person's mouth 18 to obtain a tight fit between gasket member 22 and the person's face 11.

The following step is the removing of each of the peelable protective coverings 256, 257, 266 and 267 from the exterior and interior adhesive surfaces 253, 255, 263 and 265 from each of the first and second trimmed lateral cheek flaps 250 and 260, respectively, in preparation for attaching the trimmed lateral cheek flaps 250 and 260 to the first and second trimmed adhesive perimeter lip surfaces 244 and 246 and to the person's face 11.

The fifth step is the removing of the peelable protective covering 236 from the gasket member 22 in preparation for attaching to the exterior adhesive surfaces 253 and 263 of each of the lateral cheek flaps 250 and 260 and to the person's face 11, as shown in FIG. 9 of the drawings.

The sixth step is the adhering of the exterior adhesive surfaces 253 an 263 from each of the trimmed lateral cheek flaps 250 and 260 to the first and second trimmed adhesive perimeter lip surfaces 244 and 246 of each of the trimmed first and second perimeter lips 224 and 226, respectively, of the facial mask 200.

The next step is the applying of the respiratory facial mask 200 with trimmed first and second lateral cheek flaps 250 and 260 being adhered to the trimmed first and second perimeter lips 224 and 226, and applying the trimmed interior adhesive surfaces of gasket member 22 to that of the trimmed interior adhesive surfaces 255 and 265 of each of the trimmed lateral cheek flaps 250 and 260 to the facial contours of the person's face 11 to form a peripheral airtight seal between the mask 200 and the person's face 11.

The next step is the connecting of the rotatable respiratory hose connector 270 to the first central opening 234 for expelling carbon dioxide [$CO_2$] gas out of the facial mask 200 when in use.

The last step is the connecting of the subnasal respiratory hose connector (optional-not shown) to the second central opening (optional-not shown) for making connection to a pressurized or non-pressurized gas supply 280 in order to provide respiratory therapy of air or pure oxygen to the patient.

THIRD AND FOURTH EMBODIMENTS

The operation of the third and fourth embodiments 300 and 400 of the present invention are substantially the same as the preferred embodiment 10 of the present invention.

ADVANTAGES OF THE PRESENT INVENTION

Accordingly, an advantage of the present invention is that it provides for a respiratory facial mask in the form of a kit to customize and apply a strapless respiratory face mask to fit the facial contours and shapes of various individuals when assembled and in operational use.

Another advantage of the present invention is that it provides for a respiratory facial mask that has the capability of being sealed tightly to the wearer's facial contours and skin without any skin trauma, skin irritation, or inflammatory reaction to the skin surface when in operational use by the wearer.

Another advantage of the present invention is that it provides for a respiratory facial mask that has the capability of being sealed tightly to the wearer's facial contours and skin, such that the mask wearer is able to receive pressurized or non-pressurized gases such as air, pure oxygen, anesthesia, steam-vapors, and atomized or nebulized medicines without leakage of such substances through the seal to the surrounding atmosphere or causing any decreases in gaseous pressure within the mask when in operational use by the wearer.

Another advantage of the present invention is that it provides for a respiratory facial mask and kit that is inexpensive, is simple to customize to the user's face; the facial mask can be varied in its intended use by the addition of individual components to the mask; and has a minimal number of component parts in which to assemble for proper operational use by the user.

Another advantage of the present invention is that it provides for a respiratory facial mask that is comfortable to the wearer, has an aesthetically pleasing appearance when worn, and the mask performs as a continuum of the natural skin and being capable of moving with the facial contours and skin of the user.

Another advantage of the present invention is that it provides for a respiratory facial mask having a seal cushioning material being made of flexible, viscoelastic thermoset, elastomeric and/or thermoplastic compounds and foams with double-sided tape thereon which is capable of maintaining a seal by being able to move with the facial contours and skin of the wearer, when stretching, pressing or shearing forces are applied to the respiratory mask in operational use by the wearer.

Another advantage of the present invention is that it provides for a respiratory facial mask that has the capability of being worn for longer periods of time by a user for diagnostic testing and/or medical treatment in order to achieve a higher success rate of treatment by the user when undergoing such diagnostic and medical procedures.

Another advantage of the present invention is that it provides for a respiratory facial mask that has application for use in respiratory therapy, sleep medicine, anesthesia delivery, diagnostic testing, and other medical therapeutic treatments. In addition, the respiratory facial mask can be used for high altitude breathing; military, mining, chemical, metal fabrication and other industrial applications; occupational safety and fire fighting; laboratory procedures; woodworking, metal working, paint spraying and in any environments where dust, pollen, or other air borne contaminants are present.

Another advantage of the present invention is that it provides for a strapless respiratory facial mask that requires no compression of the seal against the face so that the wearer is not uncomfortable from the pressing of the seal upon the face.

A further advantage of the present invention is that it provides for a respiratory facial mask and kit which can be easily assembled, mass produced in an automated and economical manner, and is readily affordable by the user.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. A strapless respiratory facial mask for attachment to the wearer's face, comprising:
   a) a moldable laminated gasket member including a cushioning layer and an adhesive layer for engaging the facial contours and skin of the wearer's face;
   b) said gasket member having a central opening for receiving the nose of the wearer;
   c) a nose piece member having a central section and three edges forming a generally triangular configuration for covering and surrounding the nose of the wearer;
   d) said central section of said nose piece member including a first opening for connecting to a gas supply;
   e) said nose piece member being adhered along said three edges of said nose piece member to said cushioning layer on said gasket member to form a peripheral seal; and
   f) said central section further including a second opening below said first opening and an external tubular section connected to said second opening for making a connection to a gas supply.

2. A respiratory mask in accordance with claim 1, wherein said central section of said nose piece member has a contoured shape for receiving the wearer's nose therein.

3. A respiratory mask in accordance with claim 1, wherein said tubular section further includes an annular central opening for alignment with and connection to said second opening of said central section.

4. A respiratory mask in accordance with claim 1, wherein said tubular section further includes a first end for connection to gas supply means and a second end having an auxiliary vent component therein, and said tubular section having a check valve mounted therein.

5. A respiratory mask in accordance with claim 1, wherein said adhesive layer includes double-sided adhesive film, double-sided adhesive tape, pressure-sensitive adhesive, pressure-sensitive glue, pressure-sensitive gel or other adhering material.

6. A respiratory mask in accordance with claim 1, wherein said adhesive layer includes a peelable protective covering for protecting the skin attaching surface of said adhesive layer prior to use.

7. A respiratory mask in accordance with claim 6, wherein said peelable protective covering is made of paper, cellophane, polyvinyl chloride (PVC), aluminum foil, polyethylene (PE), Teflon, silicone tapes, gels, plastic film or composites thereof.

8. A respiratory mask in accordance with claim 1, wherein said nose piece member is made from a thermoplastic material selected from the group consisting of ethylene vinyl acetate, methyl vinyl acetate, methyl acrylate, polypropylene, polyethylene, ELVAX™, polytetrafluoroethylene resin, urethanes, styrene, an acrylic, Teflon™, Sorbothane™, a carboxylate compound, or a viscoelastic thermoset compound.

9. A respiratory mask in accordance with claim 1, wherein said cushioning layer is elastic and is selected from the group consisting of elastomeric compounds such as urethanes, polyvinylchloride foam, polytetrafluoroethylene foam, acrylic foam, polystyrene foam, polyethylene foam, urethane foams, ethylvinyl acetate, silicones, rubber, neoprene, and combinations thereof.

10. A respiratory mask in accordance with claim 1, wherein said respiratory mask is made of materials for disposable or non-disposable use.

11. A strapless respiratory facial mask for attachment to the wearer's face, comprising:

a) a mask having a central section and first, second and third perimeter lips with adhesive surfaces forming a generally triangular configuration for covering and surrounding the nose of the wearer;

b) said first and second perimeter lips extending along opposite sides of the nose of the wearer, and said third perimeter lip extending across the upper lip area or extending across the bottom lip area of the wearer;

c) said central section of said mask being formed of a thermoplastic material and having a first opening for making a connection to a gas supply;

d) a moldable cushioning material connected to said first and second perimeter lips of said mask to form a peripheral sealing section for engaging the facial contours and skin of the wearer's face, and said peripheral sealing section having first and second sealing sections;

e) sealing means including a plurality of sealing strips formed of said cushioning material for attachment to one or more of said first and/or second sealing sections for providing an increased sealing area for said mask; and f) means for attaching said sealing strips to one or more of said first and/or second sealing sections of said peripheral sealing section, and for attaching said sealing strips and said peripheral sealing section of said mask to the facial contours and skin of the wearer to provide a customized mask for tightly sealing said mask and for preventing the leakage of gas therefrom.

12. A respiratory mask in accordance with claim 11, wherein said central section of said nose piece member has a contoured shape for receiving the wearer's nose therein.

13. A respiratory mask in accordance with claim 11, wherein each of said adhesive surfaces includes double-sided adhesive film, double-sided adhesive tape, pressure-sensitive adhesive, pressure-sensitive glue, pressure-sensitive gel or other adhering material.

14. A respiratory mask in accordance with claim 11, wherein each of said adhesive surfaces includes a peelable protective covering for protecting the skin attaching surface of said adhesive surface prior to use.

15. A respiratory mask in accordance with claim 14, wherein said peelable protective covering is made of paper, cellophane, polyvinyl chloride (PVC), aluminum foil, polyethylene (PE), Teflon, silicone tapes, gels, plastic film or composites thereof.

16. A respiratory mask in accordance with claim 11, wherein said thermoplastic material is selected from the group consisting of ethyl vinyl acetate, TEFLON™, methyl vinyl acetate, methyl acrylate, polypropylene, ELVAX™, polytetrafluoroethylene resin, urethanes, an acrylic or a carboxylate compound.

17. A respiratory mask in accordance with claim 11, wherein said moldable cushioning material is elastic and is selected from the group consisting of elastomeric compounds such as urethanes, polyvinylchloride foam, polytetrafluoroethylene foam, acrylic foam, polyethylene foam, urethane foams, ethylvinyl acetate, silicones, rubber, neoprene, and combinations thereof.

18. A respiratory mask in accordance with claim 11, wherein said respiratory mask is made of materials for disposable or non-disposable use.

19. A strapless respiratory facial mask for attachment to the wearer's face, comprising:

a) a mask having a central section and first, second and third perimeter lips with adhesive surfaces forming a generally triangular configuration for covering and surrounding the nose of the wearer;

b) said first and second perimeter lips extending along opposite sides of the nose of the wearer, and said third perimeter lip extending across the upper lip area or extending across the bottom lip area of the wearer; and c) said central section of said mask being formed of a thermoplastic material and having a first opening for making a connection to a gas supply.

20. A respiratory mask in accordance with claim 19, further including a moldable cushioning material connected to said first and second perimeter lips of said mask to form a peripheral sealing section for engaging the facial contours and skin of the wearer's face, and said peripheral sealing section having first and second sealing sections.

21. A respiratory mask in accordance with claim 20, further including sealing means having a plurality of sealing strips formed of said cushioning material for attachment to one or more of said first and/or second sealing sections for providing an increased sealing area for said mask.

22. A respiratory mask in accordance with claim 21, further including means for attaching said sealing strips to one or more of said first and/or second sealing sections of said peripheral sealing section, and for attaching said sealing strips and said peripheral sealing section of said mask to the facial contours and skin of the wearer to provide a customized mask for tightly sealing said mask and for preventing the leakage of gas therefrom.

23. A respiratory mask in accordance with claim 20, wherein said moldable cushioning material is elastic and is selected from the group consisting of elastomeric compounds such as urethanes, polyvinylcholoride foam, polytetrafluoroethylene foam, acrylic foam, polyethylene foam, urethane foams, ethylvinyl acetate, silicones, rubber, neoprene, and combinations thereof.

24. A respiratory mask in accordance with claim 19, wherein of said adhesive surfaces includes double-sided adhesive film, double-sided adhesive tape, pressure-sensitive adhesive, pressure-sensitive glue, pressure-sensitive gel or other adhering material.

25. A respiratory mask in accordance with claim 19, wherein of said adhesive surfaces includes a peelable protective covering for protecting the skin attaching surface of said adhesive surface prior to use.

26. A respiratory mask in accordance with claim 25, wherein said peelable protective covering is made of paper, cellophane, polyvinyl chloride (PVC), aluminum foil, polyethylene (PE), Teflon, silicone tapes, gels, plastic film or composites thereof.

27. A respiratory mask in accordance with claim 19, wherein said thermoplastic material is selected from the group consisting of ethyl vinyl acetate, TEFLON™, methyl vinyl acetate, methyl acrylate, polypropylene, ELVAX™, polytetrafluoroethylene resin, urethanes, an acrylic or a carboxylate compound.

28. A respiratory mask in accordance with claim 19, wherein said respiratory mask is made of materials for disposable or non-disposable use.

29. A method for assembling and applying a strapless respiratory face mask to a person's facial contours and skin using a kit, said kit including a mask having a moldable laminated gasket member with a peripheral sealing section including first, second and third sealing sections having a peelable protective covering thereon; and a nose piece member with a central section having first and second central openings therein and with three edges thereon, comprising the steps of:

a) molding of said nose piece member to custom fit the facial contours and skin of the person's face in preparation for adhering to said laminated gasket member;

b) trimming one or more of said first, second and third sealing sections of said peripheral sealing section to match the person's facial contours;

c) removing said peelable protective covering from said peripheral sealing section in preparation for adhering said peripheral sealing section;

d) adhering said first, second and third sealing sections of said peripheral sealing section to the person's facial contours and skin to obtain an airtight seal between said moldable laminated gasket member of said mask and the person's face;

e) molding said laminated gasket member to a person's facial contours and conforming said first and second sealing sections on said laminated gasket member to the bridge area of the person's nose and conforming said third sealing section on said laminated gasket member to the upper lip area or lower lip area of the person's face to obtain a tight fit between said laminated gasket member and the person's face; and f) adhering said nose piece member along said three edges of said nose piece member to said laminated gasket member to form a peripheral airtight seal between said nose piece member and said laminated gasket member.

30. A method for assembling and applying a strapless respiratory mask in accordance with claim 29, wherein the step of molding said nose piece member includes the step of heating said nose piece member to make said nose piece member pliable with the use of heating means.

31. A method for assembling and applying a strapless respiratory mask in accordance with claim 30, wherein said heating means is a hair blower for heating said nose piece member until the thermoplastic material is pliable.

32. A method for assembling and applying a strapless respiratory mask in accordance with claim 30, wherein said heating step includes soaking said nose piece member in near boiling hot water for 15 to 30 seconds until the thermoplastic material is pliable.

33. A method for assembling and applying a strapless respiratory mask in accordance with claim 29, further including the step of connecting a rotatable respiratory hose connector to said first central opening for expelling of carbon dioxide ($CO_2$) gas out of said facial mask when in use.

34. A method for assembling and applying a strapless respiratory mask in accordance with claim 29, further including the step of connecting a subnasal respiratory hose connector to said second central opening for making connection to a pressurized or non-pressurized gas supply to provide respiratory therapy to the wearer.

35. A method for assembling and applying a strapless respiratory face mask to a person's facial contours and skin using a kit, said kit including a mask having a central section with first, second and third perimeter lips each having adhesive surfaces having a peelable protective covering thereon, said central section having first and second center openings therein, and a pair of first and second lateral cheek flaps, each having exterior and interior adhesive surfaces thereon with a peelable protective covering thereon, comprising the steps of:

a) trimming one or more of said first, second and third perimeter lips of said mask to match the person's facial contours;

b) trimming one or more of said first and second lateral cheek flaps to match to the person's facial contours;

c) molding said first, second and third perimeter lips to a person's facial contours and conforming said first and second perimeter lips to the bridge area of the person's nose and conforming said third perimeter lip to the upper lip area or to the lower lip area of the person's face to obtain a tight fit between said first, second and third perimeter lips and the person's face;

d) removing said peelable protective coverings from said exterior and interior adhesive surfaces from each of said first and second trimmed lateral cheek flaps in preparation for attaching said trimmed lateral cheek flaps to said first and second trimmed adhesive perimeter lip surfaces and to the person's face;

e) removing said peelable protective covering from said first, second and third adhesive perimeter lip surfaces in preparation for attaching to said exterior adhesive surfaces of each of said lateral cheek flaps and to the person's face;

f) adhering said exterior adhesive surfaces from each of said trimmed lateral cheek flaps to said first and second trimmed adhesive perimeter lip surfaces of each of said trimmed first and second perimeter lips, respectively, of said mask;

g) applying said mask with said trimmed first and second lateral cheek flaps being adhered to said trimmed first and second perimeter lips; and h) applying said trimmed interior adhesive surfaces of each of said trimmed lateral cheek flaps and said first, second and third adhesive perimeter lip surfaces of said first, second and third perimeter lips to the facial contours of the person's face to form a peripheral airtight seal between said mask and the person's face.

36. A method for assembling and applying a strapless respiratory mask in accordance with claim 35, further including the step of connecting a rotatable respiratory hose connector to said first central opening for expelling of carbon dioxide ($CO_2$) gas out of said facial mask when in use.

37. A method of assembling and applying a strapless respiratory mask in accordance with claim 35, further including the step of connecting a subnasal respiratory hose connector to said second central opening for making connection to a pressurized or non-pressurized gas supply to provide respiratory therapy to the wearer.

\* \* \* \* \*